United States Patent
Kawarabata et al.

(10) Patent No.: US 8,877,063 B2
(45) Date of Patent: Nov. 4, 2014

(54) BLOOD CIRCUIT, BLOOD PURIFICATION CONTROL APPARATUS, AND PRIMING METHOD

(75) Inventors: Shigeki Kawarabata, Hiroshima (JP); Noriaki Nakagawa, Hiroshima (JP); Junya Fujii, Hiroshima (JP); Shogo Kamito, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 882 days.

(21) Appl. No.: 12/594,081

(22) PCT Filed: Mar. 25, 2008

(86) PCT No.: PCT/JP2008/000718
§ 371 (c)(1),
(2), (4) Date: Sep. 30, 2009

(87) PCT Pub. No.: WO2008/129830
PCT Pub. Date: Oct. 30, 2008

(65) Prior Publication Data
US 2010/0078385 A1    Apr. 1, 2010

(30) Foreign Application Priority Data

| Mar. 30, 2007 | (JP) | 2007-093625 |
| Mar. 30, 2007 | (JP) | 2007-094381 |
| Mar. 30, 2007 | (JP) | 2007-094382 |
| Oct. 17, 2007 | (JP) | 2007-270706 |

(51) Int. Cl.
*B01D 11/00* (2006.01)
*B01D 61/00* (2006.01)
*C02F 1/44* (2006.01)
*A61M 1/36* (2006.01)
*A61M 1/34* (2006.01)

(52) U.S. Cl.
CPC ............... *A61M 1/3643* (2013.01); *A61M 1/34* (2013.01)

USPC ........... 210/646; 210/141; 210/143; 210/209; 210/239; 210/321.71

(58) Field of Classification Search
None
See application file for complete search history.

(56) References Cited

U.S. PATENT DOCUMENTS

| 4,721,564 A | 1/1988 | Harada et al. |
| 6,110,384 A | 8/2000 | Goux et al. |

(Continued)

FOREIGN PATENT DOCUMENTS

| EP | 722744 A1 * | 7/1996 |
| EP | 1837046 | 9/2007 |

(Continued)

OTHER PUBLICATIONS

International Search Report issued Jun. 17, 2008 in International (PCT) Application No. PCT/JP2008/000718.

(Continued)

*Primary Examiner* — Dirk Bass
(74) *Attorney, Agent, or Firm* — Wenderoth, Lind & Ponack, LLP

(57) ABSTRACT

A blood circuit capable of automatically performing priming for safe treatments. The blood circuit includes: a hemofilter (56) purifying blood; a blood removal line that has an end connected to an inlet of the hemofilter (56) and that includes a first blood removal line (84), a second blood removal line (88), and a third blood removal line (89); a blood return line that has an end connected to an outlet of the hemofilter (56) and that includes the first blood return line (92) and the second blood return line (94); and an anticoagulant (bypass) line (90) reducing a difference between (a) a pressure of a priming fluid flowing in the blood removal line and (b) a pressure of the priming fluid flowing in the blood return line.

15 Claims, 26 Drawing Sheets

(56) References Cited

U.S. PATENT DOCUMENTS

| | | |
|---|---|---|
| 6,274,034 B1 | 8/2001 | Nikaido et al. |
| 6,582,604 B2 | 6/2003 | Nikaido et al. |
| 7,285,105 B2 | 10/2007 | Kim et al. |
| 7,842,001 B2 | 11/2010 | Masaoka et al. |
| 2001/0032818 A1 | 10/2001 | Nikaido et al. |
| 2003/0163077 A1 | 8/2003 | Kim et al. |
| 2005/0230314 A1 | 10/2005 | Kim et al. |
| 2005/0256442 A1* | 11/2005 | Rawles et al. ............ 604/4.01 |
| 2008/0156729 A1 | 7/2008 | Kim et al. |
| 2010/0042036 A1 | 2/2010 | Masaoka et al. |

FOREIGN PATENT DOCUMENTS

| | | |
|---|---|---|
| EP | 1982737 | 10/2008 |
| JP | 63-46703 | 9/1988 |
| JP | 64-54557 | 4/1989 |
| JP | 1-113064 | 5/1989 |
| JP | 5-14589 | 2/1993 |
| JP | 5-19076 | 5/1993 |
| JP | 5-317418 | 12/1993 |
| JP | 8-38597 | 2/1996 |
| JP | 8-191889 | 7/1996 |
| JP | 2659914 | 9/1997 |
| JP | 2000-300665 | 10/2000 |
| JP | 2000-325470 | 11/2000 |
| JP | 2002-325837 | 11/2002 |
| JP | 2003-116986 | 4/2003 |
| JP | 2003-199820 | 7/2003 |
| JP | 2004-16619 | 1/2004 |
| JP | 2004-105226 | 4/2004 |
| JP | 2004-187990 | 7/2004 |
| JP | 3695506 | 9/2005 |
| JP | 2005-296187 | 10/2005 |
| JP | 2006-175103 | 7/2006 |
| JP | 2006-255394 | 9/2006 |
| JP | 4233717 | 3/2009 |
| JP | 4335988 | 9/2009 |
| WO | 2006/073166 | 7/2006 |
| WO | 2007/091438 | 8/2007 |

OTHER PUBLICATIONS

Full Machine Translation (in English language) of JP 2006-255394 previously cited in an IDS filed on Sep. 30, 2009.
Full Machine Translation (in English language) of JP 2003-116986 previously cited in an IDS filed on Sep. 30, 2009.
Full Machine Translation (in English language) of JP 2004-105226 previously cited in an IDS filed on Sep. 30, 2009.

* cited by examiner

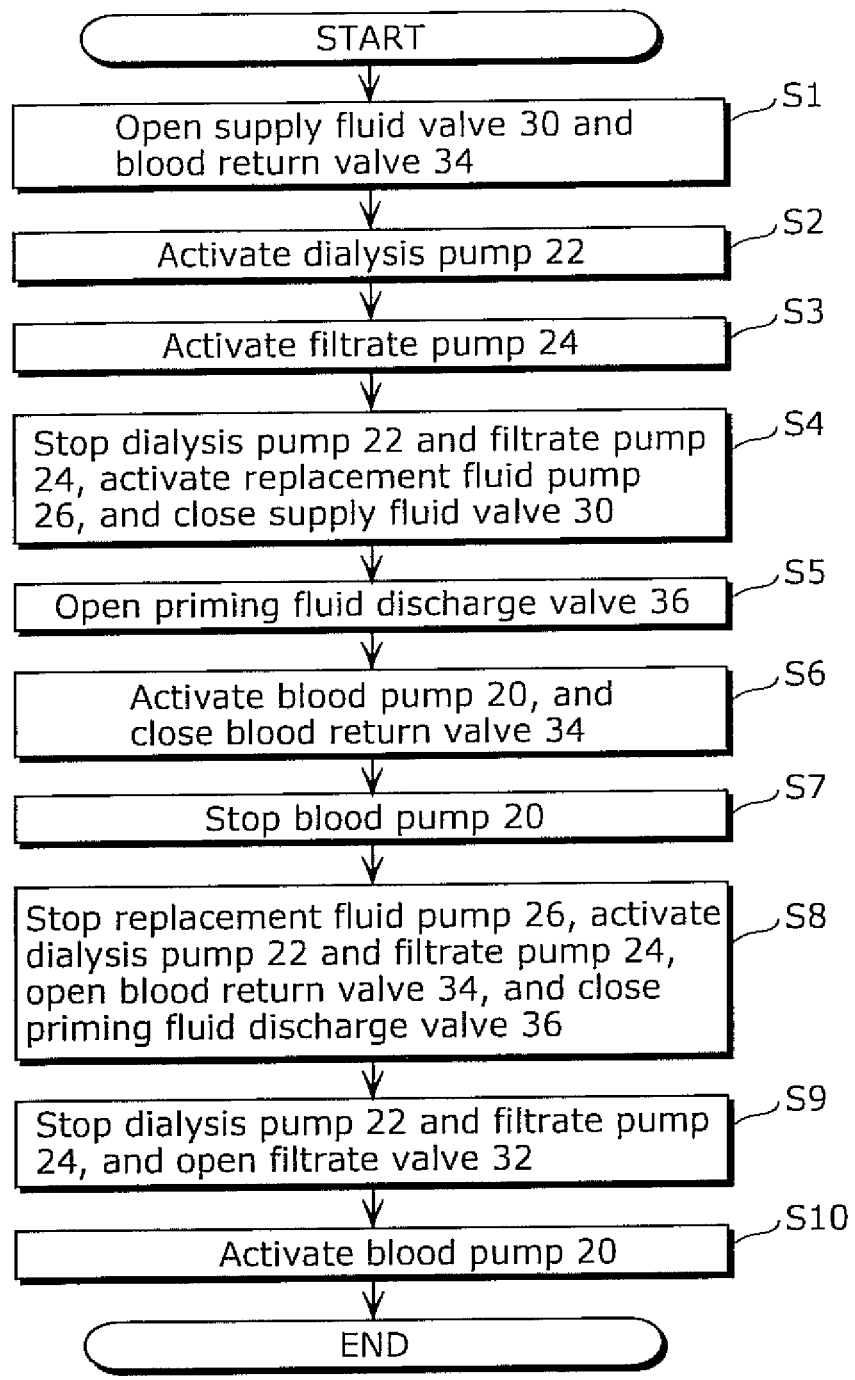

FIG. 5

| State Number | Pump | | | | Valve | | | | Supplement Line |
|---|---|---|---|---|---|---|---|---|---|
| | Blood Pump 20 | Dialysis Pump 22 | Filtrate Pump 24 | Replacement Fluid Pump 26 | Supply Fluid Valve 30 | Filtrate Valve 32 | Blood Return Valve 34 | Priming Fluid Discharge Valve 36 | |
| Initial State | Stop | Stop | Stop | Stop | Closed | Closed | Closed | Closed | First Supply Fluid Pack 50 |
| State 1 | Stop | Stop | Stop | Stop | Opened | Closed | Opened | Closed | First Supply Fluid Line 72<br>Second Supply Fluid Pack 52 |
| State 2 | Stop | Operating | Stop | Stop | Opened | Closed | Opened | Closed | Second Supply Fluid Line 74<br>Dialysate Line 76<br>Outside of Hollow Fibers in Hemofilter 56 |
| State 3 | Stop | Operating | Operating | Stop | Opened | Opened | Closed | Closed | Filtrate Line 78 |
| State 4 | Stop | Stop | Stop | Operating | Closed | Closed | Opened | Closed | Replacement Fluid Line 82 |
| State 5 | Stop | Stop | Stop | Operating | Closed | Closed | Opened | Opened | Second Blood Return Line 94<br>Second Circulation Line 98<br>Recirculation Chamber 60<br>First Blood Removal Line 84<br>Priming Fluid Discharge (Rapid Replacement Fluid) Line 86 |
| State 6 | Operating | Stop | Stop | Operating | Closed | Closed | Closed | Opened | Blood Return Chamber 58<br>First Blood Return Line 92<br>Inside of Hollow Fibers in Hemofilter 56<br>Third Blood Removal Line 89<br>Second Blood Removal Line 88 |
| State 7 | Stop | Stop | Stop | Operating | Closed | Closed | Closed | Opened | Anticoagulant (Bypass) Line 90 |
| State 8 | Stop | Operating | Operating | Stop | Closed | Opened | Opened | Closed | Filtrate Pack 54 |
| State 9 | Stop | Stop | Stop | Stop | Closed | Opened | Opened | Closed | Fluid Amount Adjustment of Filtrate Pack 54 |
| State 10 | Operating | Stop | Stop | Stop | Closed | Opened | Opened | Closed | |

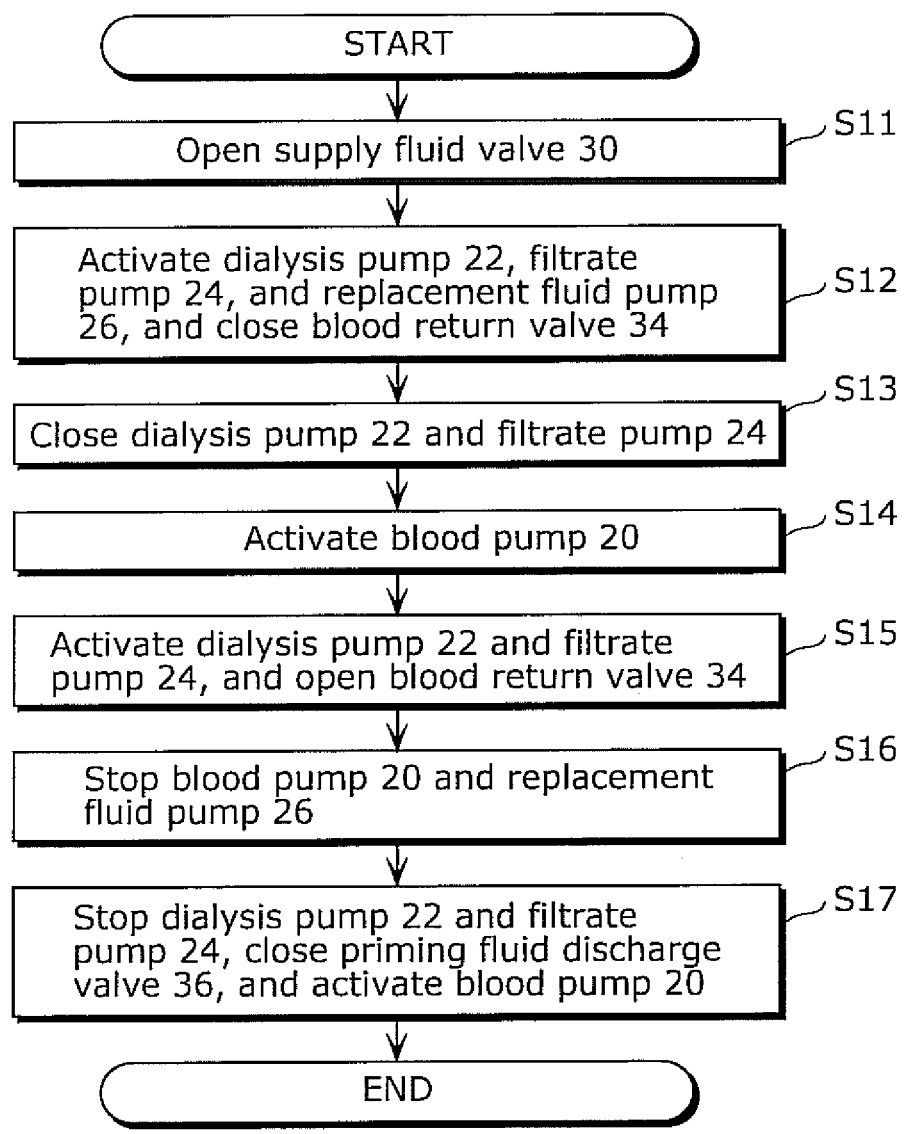

FIG. 18

| State Number | Pump (mL/min) | | | | Valve (Opened:○, Closed:×) | | | | Supplement Line |
|---|---|---|---|---|---|---|---|---|---|
| | Blood Pump 20 | Dialysis Pump 22 | Filtrate Pump 24 | Replacement Fluid Pump 26 | Supply Fluid Valve 30 | Filtrate Valve 32 | Blood Return Valve 34 | Priming Fluid Discharge Valve 36 | |
| Initial State | 0 | 0 | 0 | 0 | × | × | ○ | ○ | First Supply Fluid Pack 50 |
| State 1 | 0 | 0 | 0 | 0 | ○ | × | ○ | ○ | First Supply Fluid Line 72<br>Second Supply Fluid Pack 52 |
| State 2 | 0 | 20 | 20 | 60 | * | * | × | ○ | Second Supply Fluid Line 74<br>Dialysate Line 76<br>Replacement Fluid Line 82<br>Blood Return Chamber 58 |
| State 3 | 0 | 0 | 0 | 20 | * | * | × | ○ | First Blood Return Line 92<br>Inside of Hollow Fibers in Hemofilter 56<br>Blood Return Chamber 58 |
| State 4 | 100 | 0 | 0 | 130 | * | * | × | ○ | Third Blood Removal Line 89<br>Second Blood Removal Line 88<br>Priming Fluid Discharge<br>(Rapid Replacement Fluid) Line 86<br>Anticoagulant (Bypass) Line 90 |
| State 5 | 110 | 140 | 110 | 140 | * | * | ○ | ○ | Second Blood Return Line 94<br>First Circulation Line 96<br>Recirculation Chamber 60<br>Second Circulation Line 98<br>First Blood Removal Line 84 |
| State 6 | 0 | 130 | 100 | 0 | * | * | ○ | ○ | Outside of Hollow Fibers in Hemofilter 56<br>Filtrate Line 78 |
| State 7 | 100 | 0 | 0 | 0 | * | * | ○ | × | Outside of Hollow Fibers in Hemofilter 56<br>Filtrate Line 78<br>Recirculation |

BLOOD CIRCUIT, BLOOD PURIFICATION CONTROL APPARATUS, AND PRIMING METHOD

BACKGROUND OF THE INVENTION

1. Technical Field

The present invention relates to a blood circuit, a blood purification control apparatus, and a priming method which are used to purify blood.

2. Description of the Related Art

Patients with decreased kidney functions resulting from disease or the like receive treatments of blood purification such as dialysis from medical experts. A blood purification circuit is equipped to a blood purification control apparatus. The blood purification circuit mainly includes: a blood circuit through which blood of a patient flows; a supply fluid circuit through which dialysate or a replacement fluid flows; and a filtrate circuit through which filtrate flows. The blood purification control apparatus controls flow of fluids flowing in the blood purification circuit so as to purify the blood of the patient safely and efficiently.

In order to prepare for purifying the blood of a patient, priming is performed. In priming, a priming fluid such as physiological saline solution is filled and circulated in the blood purification circuit, so that the inside of the circuit is cleaned and air is removed from the circuit.

The blood purification circuit is fluid pathways along which blood, dialysate, a replacement fluid, and the like flow. The blood purification circuit consists of a hemofilter, chambers, needles, tubes, and the like. The hemofilter is equipment that purifies blood by exchanging substance between blood and dialysate using principles such as diffusion and ultrafiltration. Each of the chambers is an equipment that traps air bubbles (air) in a fluid flowing in a line. The needles are equipments that are connected to the blood purification circuit in performing a treatment. The needles are inserted to a blood removal position and a blood return position of shunts or the like of the patient, in order to take blood out of a patient's body and return the blood to the patient's body. Each of the tubes is provided to connection ports of the above equipments so as to connect the equipments with each other.

The chamber is originally used to trap air bubbles included in blood in the chamber when the blood runs in an appropriate direction (hereinafter, referred to as a "forward direction") in performing a treatment. Therefore, in order to fill the chamber with a priming fluid, it is necessary to (i) run the priming fluid in a forward direction when the chamber is set upside-down in comparison to the situation of a blood purification treatment, or (ii) run the priming fluid in an opposite direction when the chamber is set in the same manner as the situation of the blood purification treatment.

In addition, it is also difficult to fill the hemofilter with a priming fluid by running the priming fluid in a forward direction, due to the structure of the hemofilter. Therefore, like the chamber, in order to fill the hemofilter with a priming fluid, it is necessary to (i) run the priming fluid in a forward direction when the hemofilter is set upside-down in comparison to the situation of a blood purification treatment, or (ii) run the priming fluid in an opposite direction when the hemofilter is set in the same manner as the situation of the blood purification treatment.

Conventionally, a blood purification control apparatus and a priming method for the apparatus have been disclosed to circulate a priming fluid in a blood purification circuit in a direction opposite to a direction for a treatment, by connecting a pack storing the priming fluid to a blood return port and activating a pump to produce a pressure difference in a direction opposite to a direction for the treatment (see, for example, Japanese Unexamined Patent Application Publication No. 2006-175103).

Since the priming is performed to remove air bubbles and foreign substances from the blood purification circuit and the hemofilter (dialyzer), a priming fluid needs to have an amount enough to clean the circuit and the hemofilter. However, it is sometimes required to reduce the cleaning amount within a possible range for economical reasons or due to elimination of processing of replacing storage containers. Therefore, a cleaning operation using a so-called rinsing method, by which a cleaning fluid having only once passed through the circuit and the hemofilter is not discharged but re-circulated and then discharged, is also widely used (see, for example, Japanese Unexamined Patent Application Publication No. 5-19076)

SUMMARY OF THE INVENTION

1. Problems that Invention is to Solve

In the conventional cleaning operation using the recirculation method, an amount of a fluid sent from a replacement fluid pump to a blood circuit and an amount of a fluid sent from a blood pump to the blood circuit are vital. When the amount of the priming fluid pumped by the replacement fluid pump to the blood circuit is greater than the amount of the fluid (blood, a priming fluid, and the like) pumped by the blood pump to the blood circuit, the priming fluid flowing in the hemofilter is sometimes applied with an excessive negative pressure. Therefore, the conventional technology has a possibility that air enters the hemofilter via hollow fibers in the hemofilter. This causes a problem that the air remains in the hemofilter after priming.

The air remaining in the blood purification circuit after priming causes a risk of clotting blood in the circuit and eventually failing blood purification. In addition, if the remaining air enters a patient's body via the circuit, the air threatens a life of the patient.

On the other hand, if the amount of the fluid pumped by the replacement pump is greater than the amount of the fluid pumped by the blood pump, the hemofilter is applied with an excessive pressure, which would damage the hemofilter. As a result, it is impossible to purify blood of the patient safely and sufficiently.

A pressure produced by such a pump has a some error. Actually, the error causes pumps generally used in blood purification control apparatuses to have difficulty in keeping a balance between a positive pressure and a negative pressure applied to the hemofilter. As a result, the conventional technology has a problem of failing priming for safely performing a treatment.

In addition, the blood purification circuit has a complicated structure because the single blood purification circuit needs to realize blood purification using various methods. This complicates processes of the priming, and eventually imposes significant loads on an operator operating the blood purification circuit by hands.

Moreover, the conventional technology has a further problem. It is necessary to connect a pack storing a priming fluid to a blood return port when performing priming, and after completion of the priming, to remove the pack from the port. This is laborious processes for the operator.

Conventionally, a priming fluid is introduced to a blood circuit from a blood return port of the circuit, and discharged from a blood drawing port of the circuit. Therefore, an operator needs to connect a pack storing the priming fluid to the blood return port when performing priming, and after completion of the priming, needs to remove the pack from the blood return port because equipment for blood returning should be equipped to the blood return port. As described above, it is laborious for the operator to connect the pack storing the priming fluid to the port and then removed from the port. Furthermore, a minimum process of connecting and removing the pack is desirable from a viewpoint of hygiene.

Still further, as described above, a less amount of a fluid for completing the priming is desirable from a view of a low cost and prevention of laborious processes for replacing containers (packs).

In order to solve the above problems, an object of the present invention is to provide a blood circuit, a blood purification control apparatus, and a priming method which are capable of performing priming safely and automatically, without attaching and removing a pack storing a priming fluid for performing a treatment and without replacing the pack to another for the treatment.

The expression "in performing a treatment" means a time period from starting blood purification for a patient to completing the blood purification.

The term "hemofilter" is an equipment that purifies blood. In order to purify blood, a common hemofilter has a bundle of a large number of hollow fibers penetrated in the cylindrical inside of the hemofilter, and blood is introduced to the inside of the hollow fibers, so that via a filter formed by the hollow fibers the blood indirectly contacts with dialysate flowing in the cylindrical inside of the hemofilter. Waste products in the blood, such as urea, uric acid, creatine, and redundant water, are discharged to the dialysate, while electrolyte in the dialysate enters the blood, using principles of diffusion, ultrafiltration, and an osmotic pressure.

The term "chamber" is a gas-liquid separator that removes air bubbles and foreign substances from a fluid entering the chamber, and outputs the fluid without the air bubbles and foreign substances. A chamber in a blood purification circuit generally collects air bubbles included in a fluid flowing in the chamber to the side close to an inlet of the chamber, employing characteristics that air bubbles go up in a fluid. Thereby, the chamber traps the air bubbles in the chamber. Some "chambers" have a mesh therein to have a function of separating foreign substances from a fluid.

The term "supply fluid" is a collective term of a "replacement fluid" and a "dialysate". A typical example of the "supply fluid" is an isotonic fluid that is adjusted to have an osmotic pressure and electrolyte which are equal to those of a body fluid. The "replacement fluid" is a chemical fluid used to supply water and electrolyte into blood which have been lost from the blood passing through the hemofilter. The "dialysate" is a chemical fluid used to exchange substances between the dialysate and blood in the hemofilter.

The term "priming fluid" is a fluid used to perform priming in the blood purification control apparatus. This means that the "priming fluid" is the "supply fluid" when priming is performed using the supply fluid. It should be noted that the "replacement fluid" is often used as the "priming fluid".

The term "filtrate" is waste products and redundant water which are filtered from blood, or is dialysate after purifying blood.

The term "pump" is a device that produces a pressure to run a fluid in the blood purification circuit.

The term "valve" is a device that adjusts an amount of a fluid in the blood purification circuit at a position of the valve, and closes a fluid pathway at the position. The expression "to close a valve" means blocking a pathway of a fluid in the blood purification circuit at the position of the valve, and the expression "to open a valve" means running a fluid in the blood purification circuit at the position. For example, if a tube of the blood purification circuit is an elastic tube having some degree of elasticity, blocking of a fluid pathway can be achieved by equipping equipment for clipping the tube from the outside in order to pinch the generally opened tube from the outside.

The term "circuit" is an entire pathway in which a specific kind of a fluid flows. In more detail, a circuit is a fluid pathway in which blood, a priming fluid, a replacement fluid, or dialysate flows, and is structured by combinations of a hemofilter, chambers, branch parts, tubes, and the like. In addition, a circuit is classified into a "blood circuit" and a "supply fluid circuit", depending on a fluid flowing in the circuit in performing a treatment. The blood circuit is a circuit in which blood flows, and the supply fluid circuit is a circuit in which a replacement fluid and dialysate flow. A term "line" is a part or a branch of a circuit.

The term "forward direction" is a direction of running a fluid in a circuit in performing a treatment. On the other hand, a term "opposite direction" is a direction opposite to the forward direction. A "forward direction" of a circuit not equipped in performing a treatment and of a line in which no fluid flows will be defined later individually.

2. Means to Solve the Problems

In accordance with an aspect of the present invention for achieving the object, there is provided a blood circuit including: a hemofilter purifying blood; a blood removal line having an end connected to a blood inlet of the hemofilter; a blood return line having an end connected to a blood outlet of the hemofilter; and a bypass line reducing a difference between (a) a pressure of a priming fluid flowing in the blood removal line and (b) a pressure of the priming fluid flowing in the blood return line.

The blood circuit may include; a hemofilter purifying blood; a blood removal line having an end connected to a blood inlet of the hemofilter; a blood return line having an end connected to a blood outlet of the hemofilter; a connection line providing a priming fluid from outside of the blood circuit to the blood return line; and a bypass line reducing a difference between (a) a pressure of the priming fluid at the blood inlet of the hemofilter on the blood removal line and (b) a pressure of the priming fluid at the blood outlet of the hemofilter on the blood return line.

As described above, the blood circuit according to the aspect of the present invention includes a bypass line reducing a difference between (a) a pressure of a priming fluid flowing in the blood removal line and (b) a pressure of the priming fluid flowing in the blood return line. With the above structure, a pressure on the hemofilter is reduced more than a situation where the blood circuit does not include the bypass line. This can prevent an excessive pressure from being applied on the hollow fiber film in the hemofilter, thereby preventing the excessive pressure from damaging the function of the hemofilter. As a result, the priming can be performed without damaging the function of the hemofilter, and thereby the priming for safely performing a blood purification treatment (hereinafter, referred to also simply as a "treatment) can be automatically performed.

It is preferable that the blood removal line has a pump attachment part to which a pump is attached, that the blood return line has a valve attachment part to which a valve is attached, and that the bypass line has an end and an other end, the end being connected to one of: (a1) a position between the pump attachment part and the blood inlet of the hemofilter on the blood removal line; and (a2) a position between the blood outlet of the hemofilter and the valve attachment part on the blood return line, and the other end being connected to one of (b1) a position between an other end of the blood removal line and the pump attachment part and (b2) a position between an other end of the blood return line and the valve attachment part.

It is also preferable that the blood circuit further includes a circulation line having: an end connected to the other end of the blood removal line; and an other end connected to the other end of the blood return line. It is further preferable that the other end of the bypass line is connected to a position on the circulation line.

It is still further preferable that the blood return line has a second chamber in which air in blood exiting from the hemofilter is trapped, and that the end of the bypass line is connected to a portion of the second chamber, the portion being closer to the hemofilter. This is an example of the situation where the other end of the bypass line is connected to a position between the other end of the blood return line and the valve attachment part.

As described above, one end of the bypass line is connected to (a1) a position between the pump attachment part and the blood inlet of the hemofilter on the blood removal line or (a2) a position between the blood outlet of the hemofilter and the valve attachment part on the blood return line. And, the other end of the bypass line is connected to (b1) a position between the other end of the blood removal line and the pump attachment part or (b2) a position between the other end of the blood return line and the valve attachment part.

With the above structure, a part of the priming fluid flowing in the hemofilter can flee to the bypass line. An amount of the priming fluid flowing in the hemofilter is reduced and thereby a pressure on the hemofilter is reduced, in comparison to a situation where the blood circuit does not include the bypass line. This can prevent an excessive pressure from being applied on the hollow fiber film in the hemofilter, thereby preventing the excessive pressure from damaging the function of the hemofilter. As a result, the priming can be performed without damaging the function of the hemofilter, and thereby the priming for safely performing a blood purification treatment can be automatically performed.

It is still further preferable that the circulation line has a first chamber in which air in the priming fluid flowing from the blood removal line to the blood return line is trapped, and that the other end of the bypass line is connected to a portion of the first chamber, the portion being closer to the blood return line than to the blood removal line.

As described above, the circulation line has the first chamber that is arranged in a direction so that air bubbles in the priming fluid flowing from the blood removal line to the blood return line are trapped in the first chamber. With the above structure, after the blood purification circuit is filled with the priming fluid, the priming fluid is circulated in the blood circuit, in order to further remove air remaining in the blood circuit. In addition, the circulation line is removed and discarded before the treatment. This means that the air trapped in the first chamber is discarded together with the circulation line before the treatment. As a result, when the circulation line has the first chamber, the treatment can be performed more safely.

Furthermore, the bypass line is branched from a portion of the first chamber closer to the blood return line. Since the priming fluid flows in the hemofilter in a direction opposite to a direction for the treatment, the priming fluid flows in a direction from the blood removal line to the second chamber when priming is performed for the bypass line. When the bypass line is branched from a portion of the second chamber closer to the blood return line, air pushed from the bypass line is not trapped in the second chamber, so that air can be completely removed from the blood purification circuit. As a result, the blood purification treatment can be safely performed.

It is still further preferable that the bypass line has a resistance to a fluid pathway, the resistance being greater than a resistance of a fluid pathway of any other line in the blood circuit.

With the above structure, since the bypass line has a resistance to a fluid pathway that is greater than that of any other line, an amount of the priming fluid flowing in the bypass line is less than an amount of the priming fluid flowing in any other line. Thereby, the excessive pressure on the hemofilter can flee. As a result, the priming for safely performing a blood purification treatment can be performed.

It is still further preferable that one of the end and the other end of the bypass line has a connection part which allows the one of the end and the other end to be disconnectable from a line to which the bypass line is connected.

As described above, one of the ends of the bypass line has a connection part by which the bypass line is disconnectable from a line to which the bypass line is connected. With the above structure, while one end is connected to the line, the other disconnected end can be attached to an anticoagulant injection device, such as a syringe pump, for injecting an anticoagulant. It is common that, in performing a blood purification treatment, an anticoagulant or the like is injected to blood flowing in a blood circuit to prevent the blood from clotting. The bypass line can serve also as a circuit for injecting an anticoagulant or the like. Thereby, the treatment can be performed without laborious processes such as adding a new line.

In addition, when the other end of the bypass line is connected to the circulation line, the bypass line has a connection part by which the other end can be disconnected from the circulation line.

As described above, the other end connected to the circulation line can be disconnected from the circulation line. The other end of the bypass line is disconnected before the blood purification treatment. Since the circulation line is discarded before the treatment as previously described, unlike the other lines, it is not necessary in the treatment to close the part to which the other end of the bypass line is connected. If it is necessary to close such a part form the treatment, the process is laborious and also causes a hygiene problem such as virus contamination. Therefore, when the other end connected to the circulation line is disconnectable, the processing of shifting from the priming or recirculation to the blood purification treatment can be simplified and the treatment can be performed hygienically.

In accordance with the aspect of the present invention for achieving the object, there is provided a blood circuit including: a hemofilter purifying blood; an inflow line having an end connected to a blood inlet of the hemofilter; a discharge line having an end connected to a blood outlet of the hemofilter; and a first chamber in which air bubbles in the priming fluid flowing from an end to other end of the first chamber are trapped, the end being connected to the other end of the inflow line, and other end being connected to the other end of the discharge line.

As described above, the blood circuit includes the circulation line connecting one end of the inflow line and one end of the discharge line. Generally, the same fluid is used as the replacement fluid and the priming fluid. If the blood circuit does not include the circulation line, it is necessary to provide the priming fluid from the discharge line to the hemofilter and the chamber, so that the priming fluid runs in a direction opposite to a direction for the treatment. Here, it is necessary to exchange a line for a priming (replacement fluid) for the treatment.

When the blood circuit has the circulation line, priming can be performed for the entire blood circuit by providing the priming fluid from a line in which the replacement fluid flows in the treatment. Therefore, it is not necessary to replace the line in which the priming fluid flows in the priming to the line in which replacement fluid flows in the treatment. As a result, it is possible to simplify processes from completion of the priming to start of the treatment, and eventually perform the priming automatically.

In addition, the circulation line has the first chamber in which air bubbles in the priming fluid flowing from the inflow line to the discharge line are trapped. With the above structure, after the blood purification circuit is filled with the priming fluid, the priming fluid is circulated in the blood circuit. Thereby, air remaining in the blood circuit can be also removed. As a result, the treatment can be performed more safely.

It is still further preferable that the circulation line has a connection part disconnectable from the blood removal line and a connection part disconnectable from the blood return line.

As described above, the circulation line has a connection part that is disconnectable. With the above structure, the connection part of the circulation line can be disconnected from the blood circuit before the treatment, and then be connected to a line with an end having a needle or the like to be connected to a patient. As a result, since the circulation line has a disconnectable connection part, it is possible to simplify processes necessary from completion of the priming to start of the treatment.

It is still further preferable that the bypass line that has the one of the end and the other end disconnectably connected to the circulation line, that reduces the difference between (a) the pressure of the priming fluid flowing in the blood removal line and (b) the pressure of the priming fluid flowing in the blood return line, and that is connectable to an anticoagulant injection device injecting an anticoagulant to the blood circuit when the one of the end and the other end is disconnected from the circulation line.

As described above, the blood circuit has the bypass line having an end disconnectably connected to the circulation line. When the end of the bypass line is disconnected from the circulation line, the end can be attached to an anticoagulant injection device that injects an anticoagulant to the blood circuit. As a result, it is possible to simplify processes necessary from completion of the priming to start of the treatment.

In addition, the bypass line is used to reduce a difference between (a) a pressure of a priming fluid flowing in the blood removal line and (b) a pressure of the priming fluid flowing in the blood return line. Such a connection of the bypass line can reduce a difference in a pressure between the inlet and the outlet of the hemofilter, in comparison to a situation where the blood circuit does not have the bypass line. This can prevent an excessive pressure from being applied on the hollow fiber film in the hemofilter, thereby preventing the excessive pressure from damaging the function of the hemofilter. As a result, the priming can be performed without damaging the function of the hemofilter, and thereby the priming for safely performing a blood purification treatment can be automatically performed.

In accordance with another aspect of the present invention for achieving the object, there is provided a blood purification control apparatus controlling flow of a fluid in a blood purification circuit that includes a hemofilter purifying blood and a blood return line connected to a blood outlet of the hemofilter, the blood purification control apparatus including: a blood return valve opening and closing the blood return line; a first pump pumping a priming fluid to a part between the hemofilter and the blood return valve on the blood return line; and a first control unit configured to close the blood return valve and activate the first pump.

As described above, the blood return valve is used to activate the first pump while a flow on the blood return line is stopped. With the above structure, the priming fluid sent from the part between the hemofilter and the blood return valve on the blood return line flows from the outside of the hollow fibers to the inside of the hollow fibers in the hemofilter. This means that it is possible to run the priming fluid in the hemofilter in a direction opposite to a direction of blood in the treatment, without attaching and removing a pack storing the priming fluid. As a result, it is possible to automatically perform priming, without attaching and removing the pack storing the priming fluid.

It is preferable that the blood purification circuit further includes a blood removal line connected to a blood inlet of the hemofilter, that the blood purification control apparatus further includes a second pump (i) pumping the priming fluid to the hemofilter via the blood removal line and (ii) pumping the priming fluid out of the hemofilter via the blood removal line, and that the first control unit is configured to activate the first pump and the second pump together so that the priming fluid is pumped of the hemofilter.

As described above, by using the first pump and the second pump, an amount of the priming fluid pumped out of (taken out of) the hemofilter is less than an amount of the priming fluid pumped to (sent to) the hemofilter. As a result, by generating a redundant amount of the fluid and applying a pressure on the hemofilter using the two pumps, the priming fluid can smoothly flow in the hemofilter.

It is also preferable that the first control unit is configured to control the first pump and the second pump so that a pressure of the priming fluid pumped to by the first pump is higher than a pressure of the priming fluid pumped out by the second pump.

If a negative pressure is applied on the inside of the hollow fibers in the hemofilter, air exits from the hemofilter when air bubbles are provided in a direction from the outside of the hollow fibers to the insides. This fails to achieve the aim of the priming, in other words, fails to remove air from the blood circuit. By performing control so that a pressure of the priming fluid that is pumped to is higher than a pressure of the priming fluid that is pumped out, it is possible to prevent a negative pressure from being applied on the inside of the hollow fibers, and eventually surely remove air bubbles (air) by the priming.

It is further preferable that the blood purification control apparatus further includes a second control unit configured to open the blood return valve and activate the first pump in performing priming.

As described above, the priming for the blood return line is performed prior to the priming for the hemofilter. With the above structure, it is possible to prevent that the priming fluid filled in the hemofilter and the like is leaked via the blood return line when the blood return valve is opened. As a result, it is possible to perform priming for the blood return line and the hemofilter by using a simple control process, without complicating the blood purification circuit and the control of the circuit, for example, complicating by adding a new valve.

It is still further preferable that in the blood purification circuit, an end of the blood return line is connected via a circulation line to an end of a blood removal line, the end of the blood return line and the end of the blood removal line not being connected to the hemofilter, the blood removal line having an other end connected to the blood inlet of the hemofilter, and the circulation line having a chamber, and that the blood purification control apparatus further including: a second pump (i) pumping the priming fluid to the hemofilter via the blood return line and (ii) pumping the priming fluid out of the hemofilter via the blood return line; and a recirculation control unit configured to, after completing priming for the blood purification circuit, open the blood return valve and activate the second pump, so that the priming fluid is recirculated in the hemofilter, the blood removal line, the circulation line, and the blood return line.

As described above, when the priming for the blood purification circuit including the circulation line having the chamber is completed, the recirculation is performed. With the above structure, the priming can be completed using a small amount of the priming fluid, and air in the blood purification circuit which cannot be completely removed by the conventional technique can be trapped in the chamber in the circulation line. Then, since the circulation line is not necessary for the blood purification treatment, the circulation line is removed and discarded before the treatment. As a result, air remaining after the priming can be removed by simple processing.

It is still further preferable that the blood purification control apparatus further includes a third pump pumping the priming fluid to the hemofilter via a dialysate inlet of the hemofilter; and a third control unit configured to activate the third pump in performing priming.

It is still further preferable that the blood purification control apparatus further includes a fourth pump pumping the priming fluid out of the hemofilter via a dialysate outlet of the hemofilter, and that the third control unit is further configured to activate the fourth pump after a part of the hemofilter is filled with the priming fluid by the third pump, the part serving as a part of a dialysis circuit.

As described above, (a) the third pump for pumping the priming fluid to the hemofilter via the dialysate inlet of the hemofilter and (b) the fourth pump for pumping the priming fluid out of the hemofilter via the dialysate outlet of the hemofilter are activated sequentially. Thereby, priming can be performed for a part of the hemofilter serving as a part of the supply fluid circuit.

When the third pump pumps the priming fluid to the hemofilter via the dialysate inlet of the hemofilter along the dialysate line that is used during the treatment for sending dialysate to the hemofilter, priming is performed for the dialysate line.

When the fourth pump pumps the priming fluid out of the hemofilter via the dialysate outlet of the hemofilter along the filtrate line that is used to discharge filtrate after blood purification from the hemofilter, priming is performed for the filtrate line.

When the third pump is to be used to circulate the priming fluid in the dialysate line and the fourth pump is to be used to circulate the priming fluid in the filtrate line, the third pump and the fourth pump are activated sequentially. As a result, priming is performed for the supply fluid circuit in a series of processes.

It is still further preferable that the blood purification circuit further includes: a container in which the priming fluid pumped out of the hemofilter via the dialysate outlet is accumulated; a dialysate discharge line connecting the dialysate outlet of the hemofilter to the container; and a discharge line in which the priming fluid accumulated in the container flows to be discharged, the fourth pump circulates the priming fluid in the dialysate discharge line, and the blood purification control apparatus further including: a discharge valve opening and closing the discharge line; and a fourth control unit configured to (i) close the discharge valve and activate the third pump and the fourth pump to accumulate the priming fluid in the container, and (ii) after the accumulation, open the discharge valve to discharge a part of the priming fluid accumulated in the container.

As described above, by controlling the discharge valve (filtrate measurement clamp), the priming fluid is accumulated in a container in which the priming fluid exited from the dialysate outlet of the hemofilter is stored, and a part of the accumulated priming fluid is discharged. With the above structure, it is possible to monitor progress of the dialysis based on an amount of dialysate (filtrate) after filtration which is accumulated in the container in the treatment, and adjust an amount of the priming fluid previously accumulated in the container. Thereby, a predetermined amount of the priming fluid is previously accumulated. As a result, it is possible to detect progress of the treatment accurately more than a situation where the treatment starts when no priming fluid is in the container.

It should be noted that the present invention can be implemented not only as the above-described blood purification control apparatus, but also as a program for controlling flow of a fluid in the blood purification circuit, and as a recording medium on which the program is recorded.

In accordance with still another aspect of the present invention for achieving the object, there is provided a priming method for use in a blood purification control apparatus used for a blood purification circuit that includes a hemofilter purifying blood and a blood return line connected to a blood outlet of the hemofilter, the priming method including: a first step of closing a blood return valve on the blood return line; and a second step of sending a priming fluid to the blood return line between the blood return valve and the hemofilter.

As described above, the priming method includes a step of closing the blood return valve and a step of sending the priming fluid to the blood return line between the closed position and the hemofilter. Thereby, the priming fluid is sent to the inside of the hollow fibers in the hemofilter via the blood outlet of the hemofilter. This means that it is possible to run the priming fluid in the hemofilter in a direction opposite to a direction of blood in the treatment, without attaching and removing a pack storing the priming fluid. As a result, it is possible to automatically perform priming, without attaching and removing the pack storing the priming fluid.

It is preferable that the blood purification circuit further includes a blood removal line connected to a blood inlet of the hemofilter, and the priming method further including a third step of sending the priming fluid taken out of the hemofilter to the blood removal line.

As described above, the priming fluid is pumped out of the hemofilter. Thereby, the hemofilter can be applied with a pressure (positive pressure) of the priming fluid pumped to the hemofilter and a pressure (negative pressure) of the priming fluid pumped out of the hemofilter. As a result, by applying a positive pressure and a negative pressure on the hemofilter, the priming fluid can smoothly flow in the hemofilter.

It is also preferable that an amount of the priming fluid sent to in the second step is greater than an amount of the priming fluid taken out in the third step.

If a negative pressure is applied on the hemofilter, air exits from the hemofilter. This fails to achieve the aim of the priming, namely fails to remove air from the blood circuit. By performing control so that the positive pressure is higher than the negative pressure, the hemofilter can be applied with the positive pressure. As a result, the air removal by the priming can be surely performed.

It is further preferable that the priming method further includes a fourth step of opening the blood return line, wherein the first step is executed after the second step and the fourth step.

As described above, the priming for the hemofilter is performed, after the blood return line is opened to send the priming fluid to the blood return line. Thereby, it is possible to prevent that the priming fluid filled in the hemofilter and the like is leaked via the blood return line when the blood return valve is opened. As a result, it is possible to perform priming for the blood return line and the hemofilter by using a simple control process, without complicating the blood purification circuit and the control of the circuit, for example, complicating by adding a new valve.

It is still further preferable that the blood purification circuit further includes a circulation line that has a chamber and that connects the blood return line to a blood removal line connected to a blood inlet of the hemofilter so that the hemofilter, the blood removal line, and the blood return line forms a circularly-arranged line, and the priming method further including a fifth step of opening the blood return valve after completing priming for the blood purification circuit to run the priming fluid, so that the priming fluid is circulated in the circularly-arranged line.

As described above, when the priming for the blood purification circuit including the circulation line having the chamber is completed, the recirculation is performed. Thereby, air in the blood purification circuit, which has not been removed completely by the priming, can be trapped in the chamber in the circulation line. Then, since the circulation line is not necessary for the blood purification treatment, the circulation line is removed and discarded before the blood purification treatment. As a result, air remaining after the priming can be removed by simple processing.

It is still further preferable that the priming method further includes a sixth step of sending the priming fluid to the hemofilter via a dialysate inlet of the hemofilter.

As described above, the priming fluid is sent to the hemofilter via the dialysate inlet of the hemofilter. Thereby, priming can be performed for a line along which dialysate is sent to the hemofilter and a part of the hemofilter serving as a part of the supply fluid circuit.

It is still further preferable that the priming method further includes a seventh step of taking the priming fluid out of the hemofilter via a dialysate outlet of the hemofilter after the priming fluid is filled in a part of the hemofilter in the sixth step, the part serving as a part of a dialysis circuit.

As described above, after the priming fluid is filled in a part of the hemofilter serving as a part of the supply fluid circuit, the priming fluid is pumped out of the hemofilter via the dialysate outlet. Thereby, priming can be performed for a part of the hemofilter serving as a part of the supply fluid circuit.

As a result, in a series of processes of pumping the priming fluid from the dialysate line to the hemofilter, and pumping the priming fluid out of the hemofilter to the filtrate line, priming can be performed for the entire supply fluid circuit.

It is still further preferable that the blood purification circuit further includes: a container to which the priming fluid taken out of the hemofilter via the dialysate outlet is sent; a dialysate discharge line connecting the dialysate outlet of the hemofilter to the container; and a discharge line in which the priming fluid accumulated in the container flows to be discharged, and the priming method further including: an eighth step of sending the priming fluid taken out of the hemofilter via the dialysate outlet to the container; and a ninth step of discharging a part of the priming fluid sent to the container via the discharge line after the eighth step, so that an amount of priming fluid remaining in the container after is adjusted.

As described above, by controlling the discharge valve, the priming fluid is accumulated in a container in which the priming fluid taken out of the hemofilter via the dialysate outlet of the hemofilter is stored, and a part of the accumulated priming fluid is discharged. Thereby, it is possible to monitor progress of the dialysis based on an amount of dialysate (filtrate) after filtration which is accumulated in the container in the treatment, and adjust an amount of the priming fluid previously accumulated in the container. Thereby, a predetermined amount of the priming fluid is previously accumulated. As a result, it is possible to detect progress of the blood purification treatment accurately more than a situation where the treatment starts when no priming fluid is in the container.

3. Effects of the Invention

The blood circuit, the blood purification control apparatus, and the priming method according to the aspects of the present invention are capable of surely performing (i) cleaning of the inside of the blood circuit and (ii) removing of air bubbles from the blood circuit, without laborious processes such as attaching and removing a pack storing a priming fluid for performing a blood purification treatment or replacing the pack to another for the treatment. As a result, priming can be surely performed by simple priming processes.

BRIEF DESCRIPTION OF THE DRAWINGS

FIG. 4 is a flowchart of processes of automatic priming performed by the blood purification control apparatus when an automatic priming mode is selected, according to the first embodiment of the present invention.

FIG. 5 is a table of statues of the blood purification circuit in the respective processes of the priming according to the first embodiment of the present invention.

FIG. 17 is a flowchart of processes of automatic priming performed by the blood purification control apparatus when an automatic priming mode is selected, according to a second embodiment of the present invention.

FIG. 18 is a table of statues of a blood purification circuit in the respective processes of the priming according to the second embodiment of the present invention.

Figure 1:
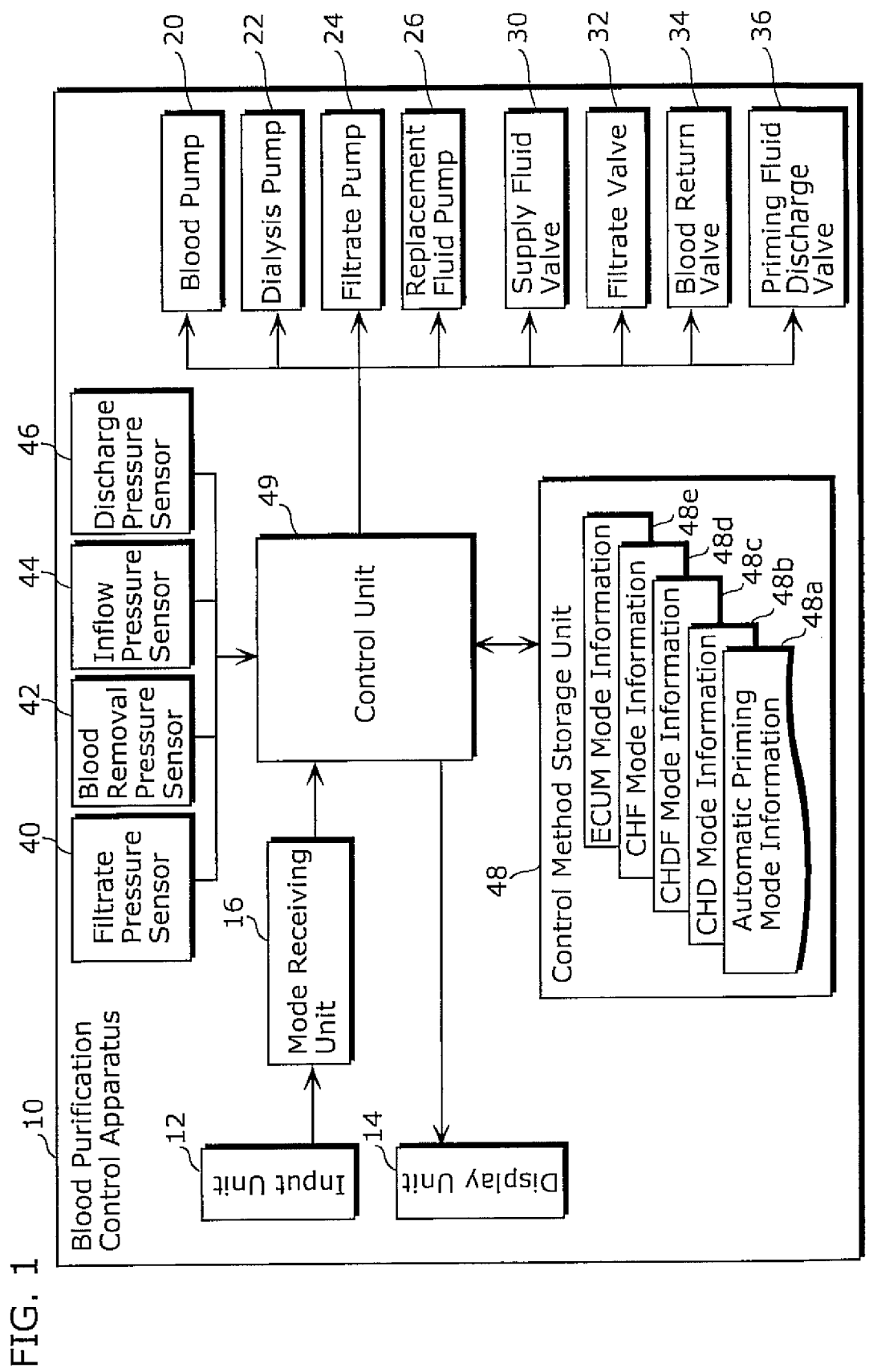
FIG. 1 is a block diagram showing a structure of a blood purification control apparatus according to a first embodiment of the present invention.

NUMERICAL REFERENCES 10 blood purification control apparatus
12 input unit
14 display unit
16 mode receiving unit
20 blood pump
22 dialysis pump
24 filtrate pump
26 replacement fluid pump
30 supply fluid valve
32 filtrate valve
34 blood return valve
36 priming fluid discharge valve
37 check valve
40 filtrate pressure sensor
42 blood removal pressure sensor
44 inflow pressure sensor
46 discharge pressure sensor
48 control method storage unit
49 control unit
50 first supply fluid pack
52 second supply fluid pack
54 filtrate pack
56 hemofilter
58 blood return chamber
60 recirculation chamber
62 supply fluid branch part
64 rapid replacement fluid branch part
66 anticoagulant branch part
68a, 68b blood removal side joint
70a, 70b blood return side joint
72 first supply fluid line
74 second supply fluid line
76 dialysate line
78 filtrate line
80 waste fluid line
82 replacement fluid line
84 first blood removal line
86 priming fluid discharge (rapid replacement fluid) line
88 second blood removal line
89 third blood removal line
90 anticoagulant (bypass) line
92 first blood return line
94 second blood return line
96 first circulation line
98 second circulation line
100, 102 waste fluid tank

DETAILED DESCRIPTION OF THE INVENTION

First Embodiment

A blood purification circuit having a blood circuit according to the first embodiment of the present invention is provided to a blood purification control apparatus that performs a priming method. The blood purification control apparatus controls pumps and valves according to a predetermined rule based on information provided from a sensor. Blood of a patient and a supply fluid flow in the blood purification circuit are under the control of the blood purification control apparatus. Thereby, the blood is purified.

First, a structure of the blood purification control apparatus is described with reference to FIG. 1.

FIG. 1 is a block diagram showing the structure of the blood purification control apparatus according to the first embodiment of the present invention.

The blood purification control apparatus 10 according to the first embodiment is an apparatus that controls priming to be automatically performed. The blood purification control apparatus 10 is also an apparatus that controls blood purification performed using various operation methods (operation modes) for a patient. In the first embodiment, the operation modes are an automatic priming mode, a Continuous Hemodialysis (CHD) mode, a Continuous Hemodiafiltration (CHDF) mode, a Continuous Hemofiltration (CHF) mode, and an Extra Corporeal Ultrafiltration Method (ECUM) mode.

The blood purification control apparatus 10 includes an input unit 12, a display unit 14, a mode receiving unit 16, a blood pump 20, a dialysis pump 22, a filtrate pump 24, a replacement fluid pump 26, a supply fluid valve 30, a filtrate valve 32, a blood return valve 34, a priming fluid discharge valve 36, a filtrate pressure sensor 40, a blood removal pressure sensor 42, an inflow pressure sensor 44, a discharge pressure sensor 46, a control method storage unit 48, and a control unit 49.

The input unit 12 is used by an operator of the blood purification control apparatus 10 to input an operation mode of the blood purification control apparatus.

The display unit 14 is a part where information is presented to the operator. An example of the display unit 14 is a monitor screen.

The mode receiving unit 16 receives information indicating the operation mode inputted by the input unit 12.

The blood pump 20 is a pump producing a pressure to take blood out of a patient. The blood pump 20 can produce the pressure not only in a direction (hereinafter, referred to as a "forward direction") of running a fluid in the blood purification circuit in performing a blood purification treatment, but also in a direction (hereinafter, referred to as an "opposite direction") opposite to the forward direction. The blood pump 20 corresponds to the "second pump" in the aspect of the present invention.

The dialysis pump 22 is a pump producing a pressure to run dialysate in the blood purification circuit. "The dialysis pump 22 corresponds to the "third pump" in the aspect of the present invention.

The filtrate pump 24 is a pump producing a pressure to run filtrate in the blood purification circuit. The filtrate pump 24 corresponds to the "fourth pump" in the aspect of the present invention.

The replacement fluid pump 26 is a pump producing a pressure to run a replacement fluid in the blood purification circuit. The replacement fluid pump 26 corresponds to the "first pump" in the aspect of the present invention.

The supply fluid valve 30 is a valve used to adjust an amount of a supply fluid that is supplied and stop supplying a supply fluid.

The filtrate valve 32 is a valve used to adjust an amount of a discharged filtrate and stop discharging a filtrate. The filtrate valve 32 corresponds to the "discharge valve" in the aspect of the present invention.

The blood return valve 34 is a valve used to adjust an amount of blood which runs from a hemofilter and returns to a patient, and to stop returning blood. The blood return valve 34 corresponds to the "blood return valve" in the aspect of the present invention.

The priming fluid discharge valve 36 is a valve provided on a pathway along which a priming fluid is discharged, and used to discharge the priming fluid. The priming fluid discharge valve 36 is also used to adjust an amount of a rapid replacement fluid that is rapidly provided to the blood purification circuit, and to stop providing the rapid replacement fluid. The rapid replacement fluid is provided when immediate supply of the replacement fluid is required.

The filtrate pressure sensor 40 is a sensor that measures a pressure applied on a line in which filtrate flows.

Each of the blood removal pressure sensor 42 and the inflow pressure sensor 44 is a sensor that measures a pressure of flowing blood not yet purified which is taken out of the patient using the blood pump 20. The blood removal pressure sensor 42 is provided to measure a pressure of blood flowing in a line close to the patient rather than the blood pump 20 that is located in an upstream in performing the treatment. Thereby, the blood removal pressure sensor 42 can detect occlusion and the like of a blood vessel of the patient or a puncture portion, for example. The inflow pressure sensor 44 is provided to measure a pressure of blood flowing in a line close to the hemofilter rather than the blood pump 20 that is located in a downstream in performing the treatment. Thereby, the inflow pressure sensor 44 can detect occlusion and the like of hollow fibers in the hemofilter, for example.

The discharge pressure sensor 46 is a sensor that measures a pressure of blood discharged from the hemofilter 56.

The control method storage unit 48 holds information regarding a control method corresponding to the operation mode provided from the blood purification control apparatus 10. The control method storage unit 48 according to the first embodiment is a storage medium in which automatic priming mode information 48a, CHD mode information 48b, CHDF mode information 48c, CHF mode information 48d, and ECUM mode information 48e are stored.

The automatic priming mode information 48a is information including a method of controlling the pumps and valves when the blood purification control apparatus 10 performs automatic priming.

Each of the CHD mode information 48b, the CHDF mode information 48c, and the CHF mode information 48d is information including a method of controlling the pumps and the valves to purify blood using a corresponding blood purification method. The ECUM mode information 48e is information including a method of controlling the pumps and the valves to remove water from blood via the hemofilter without running dialysate. The CHD mode information 48b is information including a method of controlling the pumps and the valves when Continuous Hemodialysis (CHD) is performed. The CHDF mode information 48c is information including a method of controlling the pumps and the valves when Continuous Hemodiafiltration (CHDF) is performed. The CHF mode information 48d is information including a method of controlling the pumps and the valves when Continuous Hemofiltration (CHF) is performed. The ECUM mode information 48e is information including a method of controlling the pumps and the valves when Extra Corporeal Ultrafiltration Method (ECUM) is performed.

The control unit 49 reads out, from the control method storage unit 48, information corresponding to the operation mode received by the mode receiving unit 16, and controls each pump and each valve with reference to information obtained from a pressure sensor and other sensors (not shown) based on the readout information.

The "first control unit", the "second control unit", the "third control unit", the "fourth control unit", and the "recirculation control unit" are implemented by the control unit 49 that reads out the automatic priming mode information 48a and controls each pump and each valve based on the readout automatic priming mode information 48a.

Next, a structure of the blood purification circuit provided to the blood purification control apparatus 10 to perform the various blood purification methods is described with reference to FIG. 2.

Figure 2:
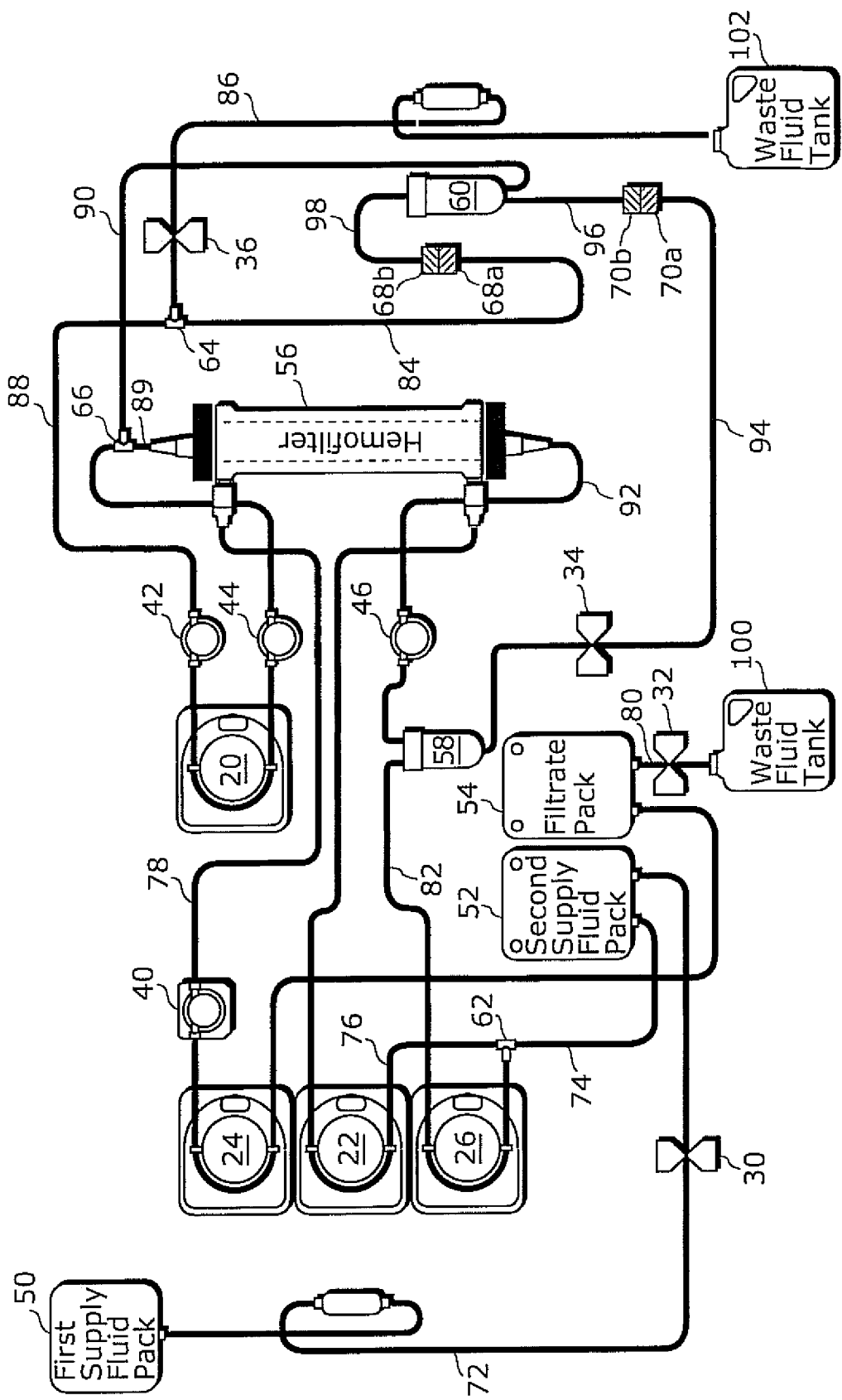
FIG. 2 is a diagram showing a structure of a blood purification circuit in performing priming and position relationships with pumps, valves, and pressure sensors of the blood purification control apparatus, according to the first embodiment of the present invention.

FIG. 2 is a diagram showing the structure of the blood purification circuit in performing priming and position relationships with the pumps, the valves, and the pressure sensors of the blood purification control apparatus, according to the first embodiment of the present invention.

In performing priming, the blood purification circuit includes a first supply fluid pack 50, a second supply fluid pack 52, a filtrate pack 54, a hemofilter 56, a blood return chamber 58, a recirculation chamber 60, a supply fluid branch part 62, a rapid replacement fluid branch part 64, an anticoagulant branch part 66, a blood removal side joint 68a, a blood removal side joint 68b, a blood return side joint 70a, a blood return side joint 70b, a first supply fluid line 72, a second supply fluid line 74, a dialysate line 76, a filtrate line 78, a waste fluid line 80, a replacement fluid line 82, a first blood removal line 84, a priming fluid discharge (rapid replacement fluid) line 86, a second blood removal line 88, a third blood removal line 89, an anticoagulant (bypass) line 90, a first blood return line 92, a second blood return line 94, a first circulation line 96, and a second circulation line 98.

For explanation of position relationships between (a) the blood purification circuit and (b) the pumps, the valves, and the sensors in the blood purification control apparatus 10, FIG. 2 also shows the blood pump 20, the dialysis pump 22, the filtrate pump 24, the replacement fluid pump 26, the supply fluid valve 30, the filtrate valve 32, the blood return valve 34, the priming fluid discharge valve 36, the filtrate pressure sensor 40, the blood removal pressure sensor 42, the inflow pressure sensor 44, and the discharge pressure sensor 46. These elements included in the blood purification control apparatus 10 have been described with reference to FIG. 1, so that details of these elements are not described again below.

The first supply fluid pack 50 is a container in which a supply fluid is firstly stored.

The second supply fluid pack 52 is a container in which a supply fluid provided from the first supply fluid pack 50 is stored.

The filtrate pack 54 is a container in which filtrate that is a fluid applied with blood purification is stored. The filtrate pack 54 corresponds to the "container" in the aspect of the present invention.

It is assumed in the first embodiment that the same kind of fluid is used as a priming fluid, a replacement fluid, and dialysate. The supply fluid provided from the first supply fluid pack 50 is temporarily stored in the second supply fluid pack 52, and then provided to another circuit in the blood purification circuit. During the blood purification treatment, the supply fluid stored in the second supply fluid pack 52 is used as a replacement fluid and dialysate. After being applied with blood purification, the supply fluid is stored as filtrate in the filtrate pack 54.

The above structure makes it possible, for example, to measure exact weights of the second supply fluid pack 52 and the filtrate pack 54 in performing the treatment. Then, if the control unit 49 obtains the measurement results, it is possible to realize automatic control of the blood purification treatment based on progress of the treatment and an amount of the supply fluid entering the patient's body.

The hemofilter 56 is an equipment that purifies blood. Regarding the hemofilter 56 shown in FIG. 2, blood enters the hemofilter 56 from a blood inlet provided at a top of the cylindrical hemofilter 56 (hereinafter, referred to also as a "cylinder"), and the blood exits from a blood outlet provided at a bottom of the cylinder to return to the patient. Furthermore, dialysate enters the hemofilter 56 from a dialysate inlet provided at a lower portion of the side of the cylinder, and the dialysate after blood purification (namely, filtrate) exits from a dialysate outlet provided at an upper portion of the side of the cylinder.

In FIG. 2, the area surrounded by a dotted line in the hemofilter 56 schematically shows the inside of hollow fibers which forms a pathway of blood, and the outside of the area schematically shows the outside of the hollow fibers which forms a pathway of dialysate. The area surrounded by the dotted line in the hemofilter 56 is a part of the blood circuit. Here, a direction from the blood inlet to the blood outlet is a forward direction. On the other hand, the outside of the area is a part of the supply fluid circuit. Here, a direction from the dialysate inlet to the dialysate outlet is a forward direction.

The blood return chamber 58 is a place where air bubbles included in blood discharged from the hemofilter 56 are trapped and where the returning blood is mixed with a replacement fluid. This blood return chamber 58 corresponds to the "second chamber" in the aspect of the present invention.

The recirculation chamber 60 is a chamber that traps, when performing recirculation, air bubbles remaining in the blood circuit and the hemofilter after performing priming. Here, the "recirculation" means circulating of a priming fluid in the blood circuit during a period from completion of filling the blood purification circuit with the priming fluid to start of the blood purification treatment for the patient.

These chambers can trap air bubbles included in a fluid flowing in a forward direction, but cannot trap air bubbles in a fluid flowing in an opposite direction. Therefore, firstly a fluid runs in the opposite direction to remove all air bubbles from the chambers, thereby priming the chambers. Then, the priming fluid is circulated in a forward direction to remove small air bubbles caused in the circulation.

The supply fluid branch part 62 is a part where a supply fluid is separated into dialysate and a replacement fluid.

The rapid replacement fluid branch part 64 is a part where a replacement fluid and the like are rapidly mixed to the blood taken out of the patient.

The anticoagulant branch part 66 is a part where an anticoagulant is mixed to the blood taken out of the patient.

The blood removal side joints 68a and 68b are joint members that can be connected to and disconnected from each other. In performing priming, the blood removal side joints 68a and 68b are connected to each other as shown in FIG. 2.

On the other hand, in performing a blood purification treatment, the blood removal side joint 68a is disconnected from the blood removal side joint 68b. Furthermore, in performing the treatment, the blood removal side joint 68a is connected not to the blood removal side joint 68b, but to an equipment used to take blood out of the patient. An example of the equipment connected to the blood removal side joint 68a is a needle inserted to the patient. The blood of the patient is introduced to the blood purification circuit via the equipment such as the needle.

The blood return side joints 70a and 70b are joint members that can be connected to and disconnected from each other. In performing priming, the blood return side joints 70a and 70b are connected to each other as shown in FIG. 2.

The blood return side joints 70a and 70b are joint members that can be connected to and disconnected from each other. Furthermore, in performing the treatment, the blood return side joint 70a is connected not to the blood return side joint 70b, but to an equipment used to return blood to the patient's body. An example of the equipment connected to the blood return side joint 70a is a needle inserted to the patient. Purified blood is returned to the patient's body via the needle.

Thereby, the equipment connected to each of the blood removal side joint 68a and the blood return side joint 70a is different between in performing the treatment and in performing priming. Therefore, the blood removal side joint 68a has a shape connectable to both of the blood removal side joint 68b and the equipment used to take blood out of the patient. The blood return side joint 70b has a shape connectable to both of the blood return side joint 70a and the equipment used to return blood to the patient's body.

Since the blood removal side joint 68*a* and the blood return side joint 70*a* have such shapes, the operator of the blood purification control apparatus and the blood purification circuit can easily switch the recirculation following the priming to the blood purification treatment.

The first supply fluid line 72 is a line in which the supply fluid flows from the first supply fluid pack 50 to the second supply fluid pack 52 in performing the treatment. As shown in FIG. 2, the supply fluid valve 30 is provided on the first supply fluid line 72.

The second supply fluid line 74 is a line in which a supply fluid flows from the second supply fluid pack 52 to the supply fluid branch part 62 in performing the treatment.

The dialysate line 76 is a line in which dialysate flows from the supply fluid branch part 62 to the dialysate inlet of the hemofilter 56 in performing the treatment. A dialysis pump attachment part to which the dialysis pump 22 is attached is provided on the dialysate line 76. The dialysis pump 22 is attached to the dialysis pump attachment part as shown in FIG. 2.

The filtrate line 78 is a line in which filtrate flows from the dialysate outlet of the hemofilter 56 to the filtrate pack 54. A filtrate pump attachment part to which the filtrate pump 24 is attached is provided on the filtrate line 78. The filtrate pump 24 is attached to the filtrate pump attachment part as shown in FIG. 2. The filtrate line 78 corresponds to the "dialysate discharge line" in the aspect of the present invention.

The waste fluid line 80 is a line in which filtrate is discharged from the filtrate pack 54 where the filtrate is stored. The filtrate valve attachment part to which the filtrate valve 32 is attached is provided on the waste fluid line 80. The filtrate valve 32 is attached to the filtrate valve attachment part as shown in FIG. 2.

The filtrate valve 32 is closed in performing the treatment so that filtrate does not flow in the waste fluid line 80. The filtrate valve 32 is opened after the treatment so that the filtrate flows from the filtrate pack 54 to an open end of the waste fluid line 80. The direction of running the filtrate from the filtrate pack 54 to the open end is called a "forward direction" of the waste fluid line 80.

The replacement fluid line 82 is a line in which a replacement fluid flows from the supply fluid branch part 62 to the blood return chamber 58 in performing the treatment. The replacement fluid line 82 corresponds to the "connection line" in the aspect of the present invention. The replacement fluid line 82 that provides the replacement fluid to the blood return line can prevent from arranging or replacing the hemofilter 56 to a different position in performing the treatment.

A replacement fluid pump attachment part to which the replacement fluid pump 26 is attached is provided on the replacement fluid line 82. The replacement fluid pump 26 is attached to the replacement fluid pump attachment part as shown in FIG. 2.

The first blood removal line 84 is a line in which blood not yet purified flows from the blood removal side joint 68*a* to the anticoagulant branch part 66 in performing the treatment.

The priming fluid discharge (rapid replacement fluid) line 86 having an open end that is an outlet from which air included in the blood purification circuit and the priming fluid are discharged in performing priming. The priming fluid discharge (rapid replacement fluid) line 86 also serves, in performing the treatment, as a line in which a replacement fluid rapidly flows when the replacement fluid needs to be supplied to blood in the blood purification treatment. In other words, in performing the treatment, the priming fluid discharge (rapid replacement fluid) line 86 connects a rapid replacement fluid pack (not shown) for rapid replacement to the rapid replacement fluid branch part 64. Therefore, the rapid replacement fluid flows from the rapid replacement fluid pack (not shown) to the rapid replacement fluid branch part 64. On the other hand, in performing priming, the priming fluid discharge (rapid replacement fluid) line 86 serves as a line for discharging the priming fluid, having one end connected to the rapid replacement fluid branch part 64 and the other end opened.

A priming fluid discharge valve attachment part to which the priming fluid discharge valve 36 is attached is provided on the priming fluid discharge (rapid replacement fluid) line 86. The priming fluid discharge valve 36 is attached to the priming fluid discharge valve attachment part as shown in FIG. 2.

The second blood removal line 88 is a line in which blood not yet purified flows from the rapid replacement fluid branch part 64 to the anticoagulant branch part 66 in performing the treatment. A blood pump attachment part to which is the blood pump 20 is attached provided on the second blood removal line 88. The blood pump 20 is attached to the blood pump attachment part as shown in FIG. 2.

The third blood removal line 89 is a line in which blood not yet purified flows from the anticoagulant branch part 66 to the blood inlet of the hemofilter 56 in performing the treatment.

The anticoagulant (bypass) line 90 is a line which bypasses a line connected to the blood inlet of the hemofilter 56 and a line connected to the blood outlet of the hemofilter 56 in performing priming, in order to prevent an excessive pressure from being applied to the hemofilter 56. The anticoagulant (bypass) line 90 corresponds to the "bypass line" in the aspect of the present invention.

An amount of a priming fluid flowing in the hemofilter 56 is controlled by operating the pumps.

In the first embodiment, the replacement fluid pump 26 pumps (sends) a priming fluid to the hemofilter 56, and the blood pump 20 pumps (takes) the priming fluid out of the hemofilter 56. The operation of the pumps has errors, irregularity, and the like. Therefore, an amount or a pressure of the priming fluid pumped by the replacement fluid pump 26 is set greater than an amount or a pressure of the priming fluid pumped out by the blood pump 20. Such control of the pumps enables the priming fluid to smoothly flow in the hemofilter 56, thereby achieving the priming of the hemofilter 56.

Furthermore, errors and irregularity in the pump operation sometimes would cause an excessive pressure on the hemofilter 56. An excessive pressure damages the hollow fibers in the hemofilter 56, possibly causing a leakage or the like. As a result, the priming fails. In order to address the problem, a bypass technique is employed to shorten the blood circuit using a line with a great resistance to a fluid pathway in performing priming. Thereby, an excessive pressure on the hemofilter 56 can be prevented, and eventually more reliable priming can be achieved.

The line with a great resistance to a fluid pathway is implemented by a tube with a diameter smaller than that of a tube of any other line. It should be noted that a general anticoagulant line used in performing a blood purification treatment is thinner than a tube of any other line.

In performing the treatment, the above anticoagulant (bypass) line 90 serves as a line in which an anticoagulant flows from an anticoagulant injection device (not shown) provided at an end of the anticoagulant (bypass) line 90 to the anticoagulant branch part 66. In more detail, the anticoagulant injection device used in performing the treatment is connected, in performing priming, to an end of the anticoagulant (bypass) line 90 which is connected to an outlet of the recirculation chamber 60.

Here, the anticoagulant injection device is a device that injects an anticoagulant to the blood circuit. Examples of the anticoagulant injection device are a syringe storing a solution added with heparin, a syringe pump attached with such a syringe, and the like.

Generally, a line for injecting an anticoagulant is a tube having an inner diameter that is approximately one third of an inner diameter of a tube of a line in which blood or a supply fluid flows. Therefore, the bypass line used in performing priming can be used also as the anticoagulant (bypass) line 90 in performing the treatment. Therefore, it is possible to efficiently perform priming for the hemofilter 56, without further complicating the blood purification circuit, for example, complicating by adding a new line for injecting an anticoagulant in performing the blood purification treatment.

The first blood return line 92 is a line in which blood flows from the blood outlet of the hemofilter 56 to an inlet of the blood return chamber 58 in performing the treatment.

The second blood return line 94 is a line in which blood flows from an outlet of the blood return chamber 58 to the blood return side joint 70a in performing the treatment. Furthermore, a blood return valve attachment part to which the blood return valve 34 is attached is provided on the second blood return line 94. The blood return valve 34 is attached to the blood return valve attachment part as shown in FIG. 2.

The first circulation line 96 is a line in which a priming fluid flows from the blood removal side joint 68b to a blood inlet of the recirculation chamber 60 in performing priming. The first circulation line 96 is not equipped in the blood purification circuit in performing the blood purification treatment. In the first circulation line 96, the direction from the blood removal side joint 68b to the blood inlet of the recirculation chamber 60 is called a forward direction.

The second circulation line 98 is a line in which a priming fluid flows from a blood outlet of the recirculation chamber 60 to the blood return side joint 70b in performing priming. The second circulation line 98 is not equipped in the blood purification circuit in performing the blood purification treatment. In the second circulation line 98, the direction from the blood outlet of the recirculation chamber 60 to the blood return side joint 70b is called a forward direction.

In the above-described blood purification circuit according to the first embodiment, the blood circuit consists of a "blood removal line", the inside of the hollow fibers in the hemofilter 56, a "blood return line", the priming fluid discharge (rapid replacement fluid) line 86, and the anticoagulant (bypass) line 90.

The "blood removal line" consists of the blood removal side joint 68a, the first blood removal line 84, the rapid replacement fluid branch part 64, the second blood removal line 88, the anticoagulant branch part 66, and the third blood removal line 89.

The "blood return line" consists of the first blood return line 92, the blood return chamber 58, the second blood return line 94, and the blood return side joint 70a.

The supply fluid circuit consists of the first supply fluid pack 50, the first supply fluid line 72, the second supply fluid pack 52, the second supply fluid line 74, the replacement fluid line 82, the dialysate line 76, the outside of the hollow fibers in the hemofilter 56, the filtrate line 78, the filtrate pack 54, and the waste fluid line 80. Here, the replacement fluid line 82 may be included in the blood circuit.

A circulation circuit consists of the blood removal side joint 68b, the first circulation line 96, the recirculation chamber 60, the second circulation line 98, and the blood return side joint 70b. This circulation circuit corresponds to the "circulation line" in the aspect of the present invention. The recirculation chamber 60 corresponds to the "first chamber" or the "chamber" in the aspect of the present invention.

Each of the waste fluid tanks 100 and 102 in FIG. 2 is a tank storing the priming fluid running out from an open end of the blood purification circuit in performing priming.

The above has described the structure of the blood purification circuit according to the first embodiment.

As described above, priming of such a complicated circuit needs complicated processes. Priming operated by hands is not merely laborious but also would cause errors in the operation. Therefore, use of an automatic priming mode can prevent laborious processes of the operator and risks of operation errors, thereby achieving reliable priming for safely performing blood purification.

The processing of the automatic priming is described with reference to FIG. 3 to FIG. 15.

Figure 3:
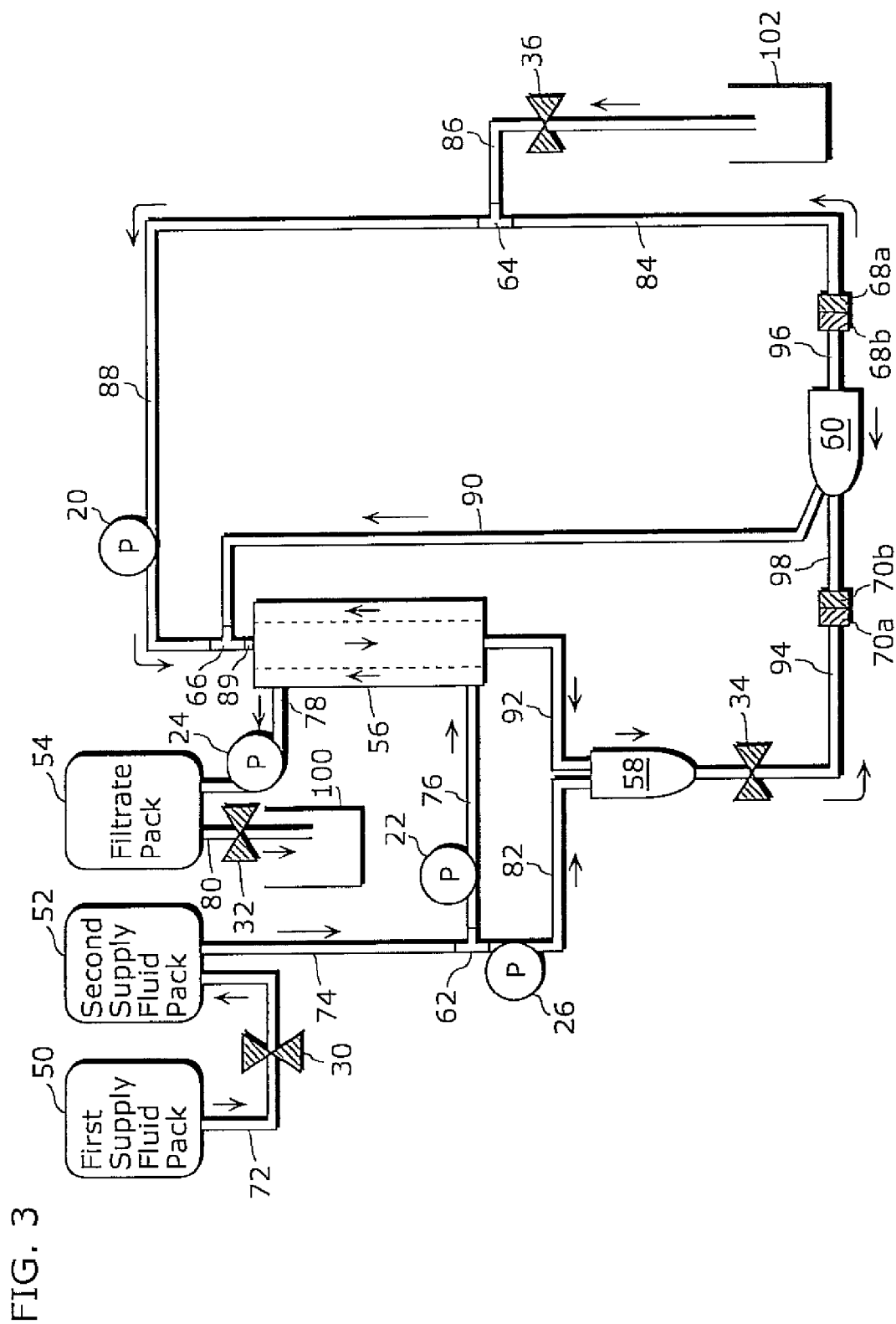
FIG. 3 is a simplified diagram showing the structure of the blood purification circuit in performing priming and the position relationships with the pumps, the valves, and the pressure sensors of the blood purification control apparatus, according to the first embodiment of the present invention.

FIG. 3 is a simplified diagram showing the structure of the blood purification circuit in performing priming and position relationships with the pumps, the valves, and the pressure sensors of the blood purification control apparatus 10, according to the first embodiment of the present invention. Arrows in FIG. 3 show forward directions of respective lines.

FIG. 3 does not show the pressure sensors seen in FIG. 2. The same reference numerals of FIG. 2 are assigned to the identical element of FIG. 3. Therefore, the identical elements are not explained again below. Although the recirculation chamber 60 is seen as lying for simplifying FIG. 3, the recirculation chamber 60 is actually arranged in the blood purification control apparatus 10 in order to have the blood inlet (connected to the first circulation line 96) to be situated top.

FIG. 4 is a flowchart of processing of the automatic priming performed by the blood purification control apparatus 10 when the automatic priming mode is selected in the first embodiment.

FIG. 4 shows processing performed by the control unit 49 to control each pump and each valve of the blood purification control apparatus 10, when the mode receiving unit 16 receives the selection of the automatic priming mode inputted by the operator using the input unit 12 and the control unit 49 reads out the automatic priming mode information 48a from the control method storage unit 48 and performs the automatic priming mode based on the readout automatic priming mode information 48a.

FIG. 5 is a table of statues of the blood purification circuit in the respective processes of the priming according to the first embodiment. Each of FIG. 6 to FIG. 15 is a circuit diagram showing a state of the blood purification circuit in each corresponding process of the priming.

The following describes each process in FIG. 4, and also describes a state of the blood purification circuit of each corresponding process with reference to FIG. 5 to FIG. 15.

In the initial state, it is assumed that the blood purification control apparatus 10 is provided with the blood purification circuit in the manner as shown in FIGS. 2 and 3, and that a priming fluid is stored only in the first supply fluid pack 50. In addition, as shown in the initial state in FIG. 5, it is assumed that all pumps stop and all valves are opened in the blood purification control apparatus 10.

Figure 6:
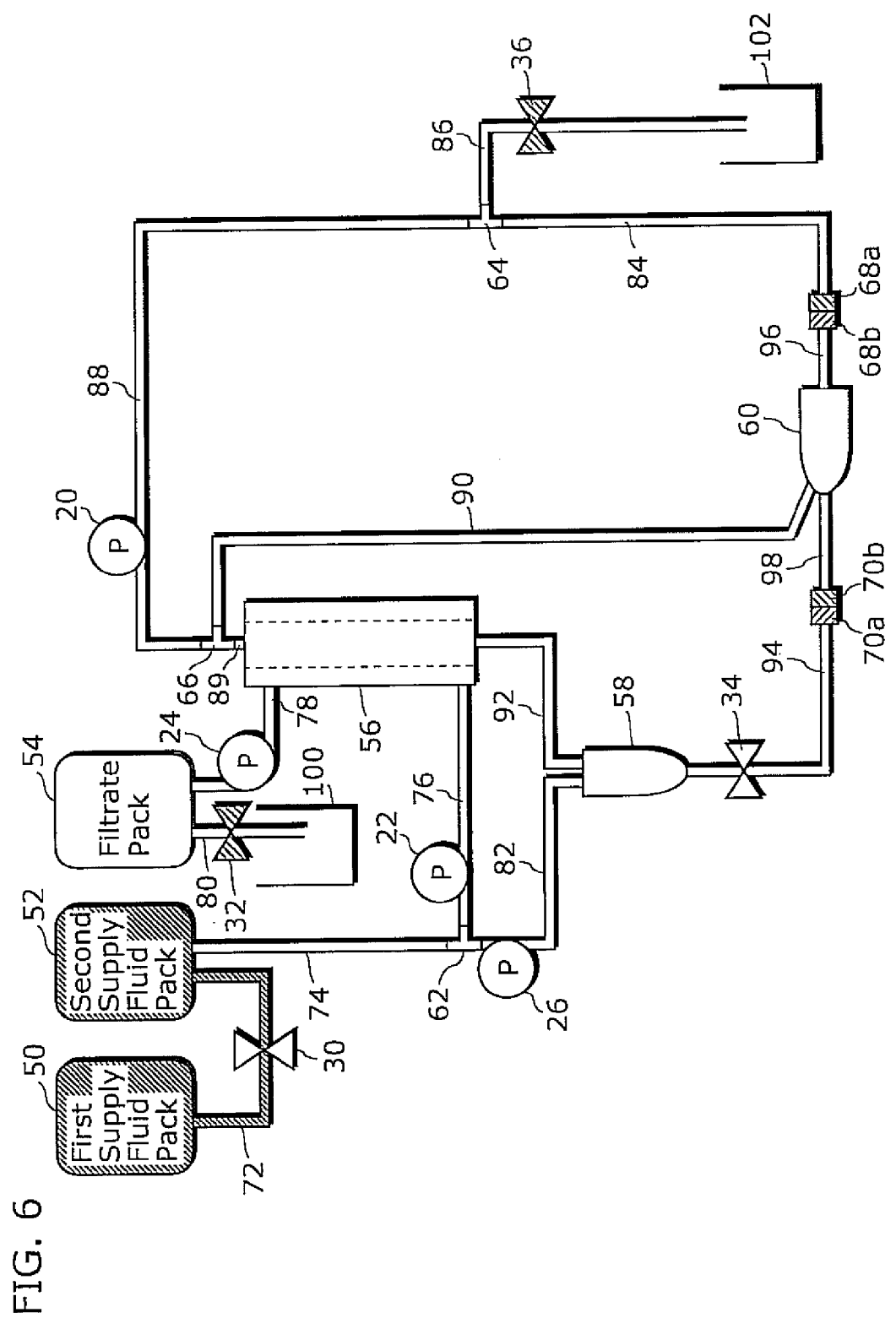
FIG. 6 is a diagram showing a state 1 in the states of the priming of the blood purification circuit according to the first embodiment of the present invention.

The control unit 49 opens the supply fluid valve 30 and the blood return valve 34 (51). Thereby, the state of the blood purification circuit becomes the state 1 in FIG. 5 in which the first supply fluid line 72 and the second supply fluid pack 52 are filled with the priming fluid (hereinafter in the explanation of the processes of priming, referred to simply as a "fluid"). The state 1 of the blood purification circuit is shown in FIG. 6. This step (process) of opening the blood return valve 34 is a step of opening the blood return line, which corresponds to the "fourth step" in the aspect of the present invention.

Here, FIG. 6 shows the state 1 in the states of the blood purification circuit in performing priming according to the first embodiment. In FIG. 6, a hatched area in the blood purification circuit shows a part where the fluid is filled (namely, the priming has been done). On the other hand, areas not hatched show parts where the fluid has not yet been filled (namely, the priming has no yet been done). In addition, in FIG. 6, hatched valves show closed valves, and valves not hatched show open valves.

The hatching in the blood purification circuit and the valves in FIG. 6 shows the above-described situations also in FIGS. 7 to 15. Therefore, the explanation of the hatching in FIGS. 7 to 15 is not given again below.

Furthermore, in FIG. 6, all pumps are not shown hatched. This means that all pumps stop. Likewise, each pump that stops is not shown hatched and each pump that is activated is shown hatched in FIGS. 7 to 15. The hatching in pumps is explained above, so that it is not explained again for each figure.

Now, the description is given referring back to FIG. 4.

Figure 7:
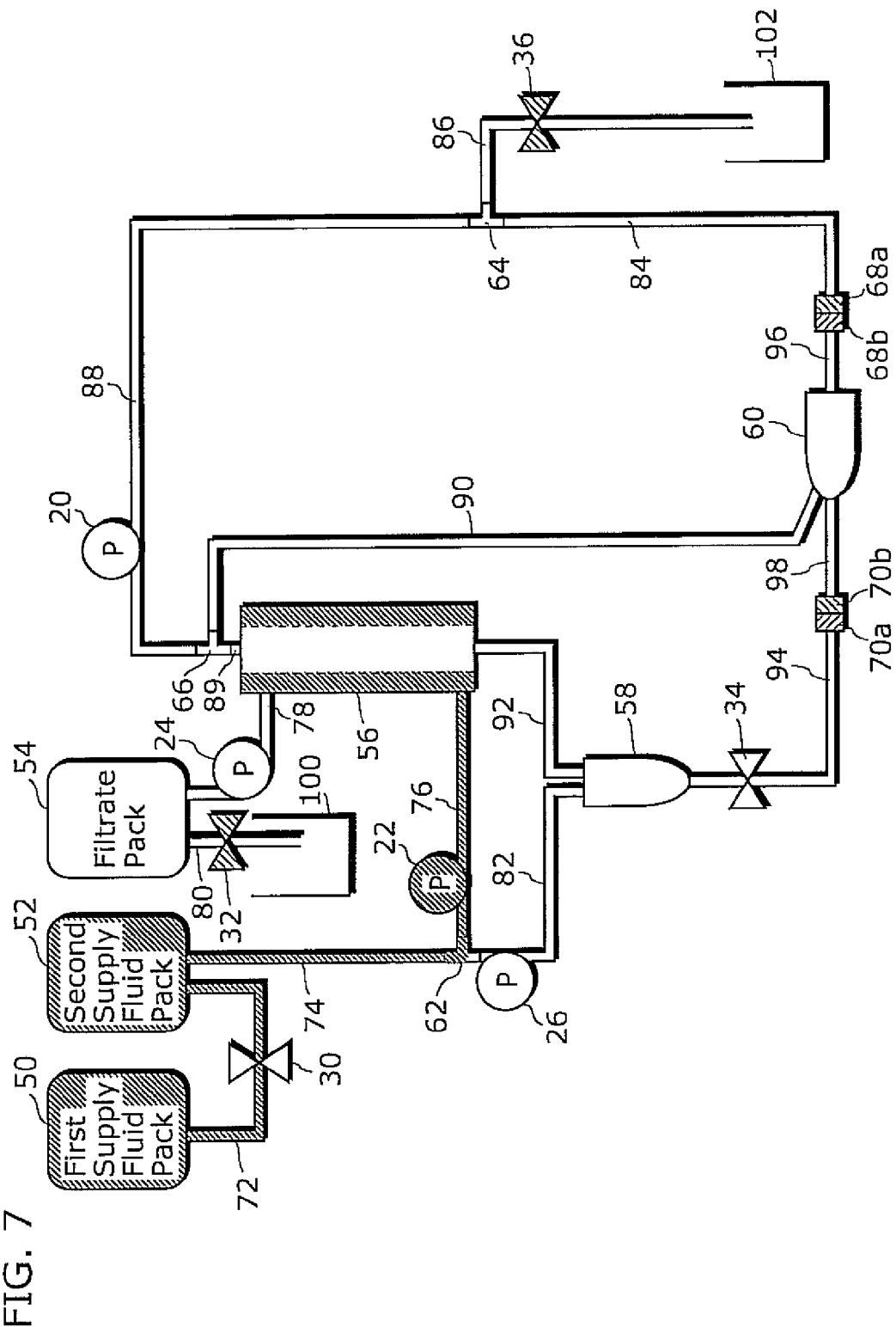
FIG. 7 is a diagram showing a state 2 in the states of the priming of the blood purification circuit according to the first embodiment of the present invention.

The control unit 49 activates the dialysis pump 22 (S2). Thereby, the state of the blood purification circuit becomes the state 2 in FIG. 5 in which the second supply fluid line 74, the dialysate line 76, the outside of the hollow fibers in the hemofilter 56 (serving as a part of the supply fluid circuit) are filled with the fluid. The state 2 of the blood purification circuit is shown in FIG. 7. This step (process) of activating the dialysis pump 22 is a step of pumping (sending) the priming fluid to the hemofilter 56 via the dialysate inlet of the hemofilter 56, which corresponds to the "sixth step" in the aspect of the present invention.

Figure 8:
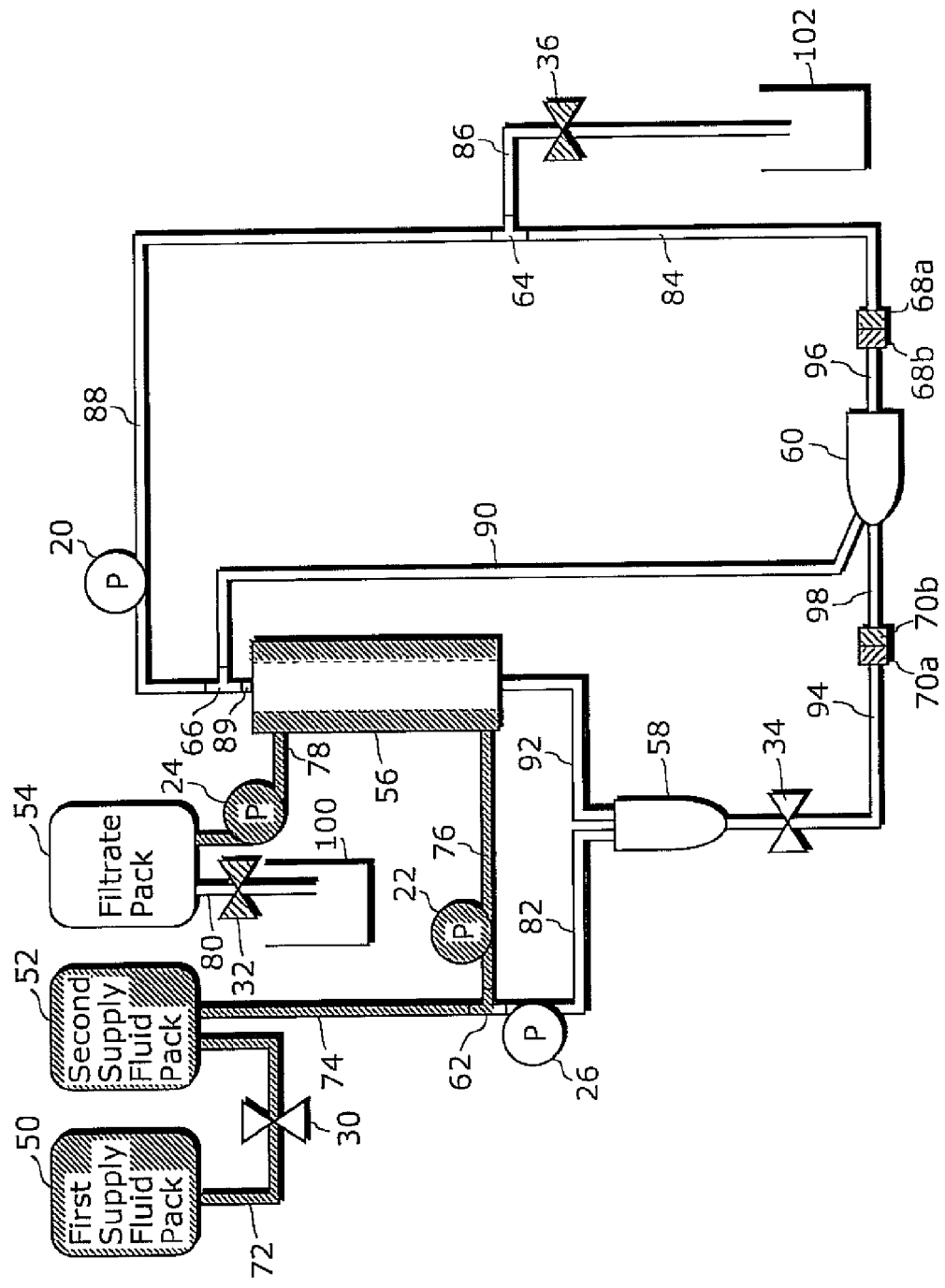
FIG. 8 is a diagram showing a state 3 in the states of the priming of the blood purification circuit according to the first embodiment of the present invention.

The control unit 49 activates the filtrate pump 24 (S3). Thereby, the state of the blood purification circuit becomes the state 3 in FIG. 5 in which the filtrate line 78 is filled with the fluid. The state 3 of the blood purification circuit is shown in FIG. 8. This step (process) of activating the filtrate pump 24 is a step of pumping the priming fluid out of the hemofilter 56 via the dialysate outlet of the hemofilter 56, after filling the priming fluid in a part of the hemofilter 56 serving as a part of the dialysis circuit. This step corresponds to the "seventh step" in the aspect of the present invention.

The control unit 49 that activates the dialysis pump 22 (S2) to fill the priming fluid in the part of the hemofilter 56 serving as a part of the dialysis circuit as shown in FIG. 7 and then activates the filtrate pump 24 (S3) corresponds to the "third control unit" in the aspect of the present invention.

Figure 9:
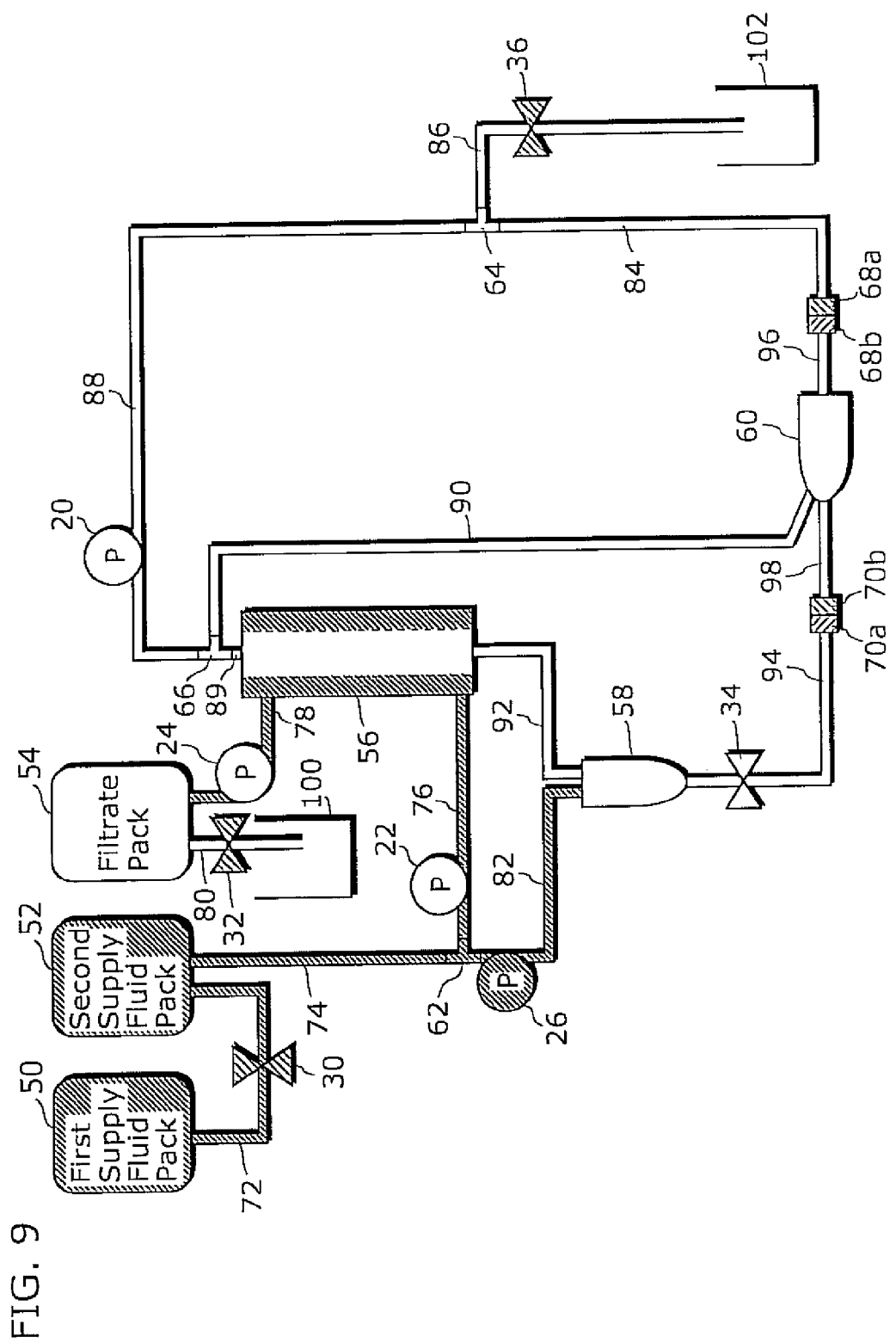
FIG. 9 is a diagram showing a state 4 in the states of the priming of the blood purification circuit according to the first embodiment of the present invention.

Then, the control unit 49 stops the dialysis pump 22 and the filtrate pump 24, activates the replacement fluid pump 26, and closes the supply fluid valve 30 (S4). Thereby, the state of the blood purification circuit becomes the state 4 in FIG. 5 in which the replacement fluid line 82 is filled with the fluid. The state 4 of the blood purification circuit is shown in FIG. 9. The control unit 49 that activates the replacement fluid pump 26 when the blood return valve 34 is opened corresponds to the "second control unit" in the aspect of the present invention. This step (process) of activating the replacement fluid pump 26 corresponds to the "second step" in the aspect of the present invention.

The above steps fill the priming fluid in the supply fluid circuit except the filtrate pack 54. Subsequently, the priming of the blood circuit starts.

Figure 10:
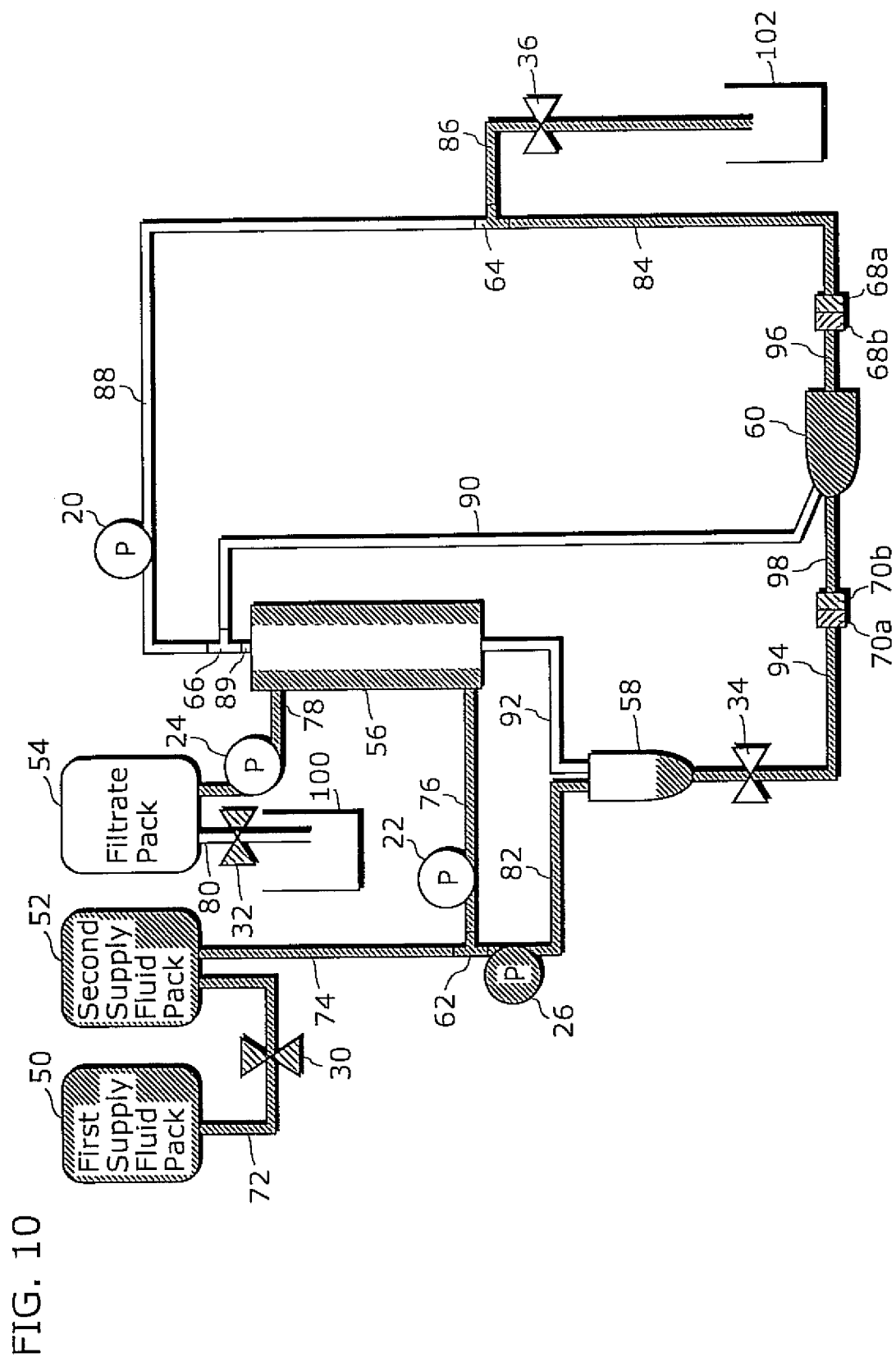
FIG. 10 is a diagram showing a state 5 in the states of the priming of the blood purification circuit according to the first embodiment of the present invention.

When the replacement fluid line 82 is filled with the fluid and the fluid reaches a supply fluid inlet of the blood return chamber 58, the control unit 49 opens the priming fluid discharge valve 36 (S5). Thereby, the state of the blood purification circuit becomes the state 5 in FIG. 5 in which the second blood return line 94, the second circulation line 98, the recirculation chamber 60, the first circulation line 96, the first blood removal line 84, the priming fluid discharge (rapid replacement fluid) line 86 are filled with the fluid. The state 5 of the blood purification circuit is shown in FIG. 10. Here, since the fluid flows in a forward direction, air is left in the blood return chamber 58 in this state although the fluid enters the blood return chamber 58.

Figure 11:
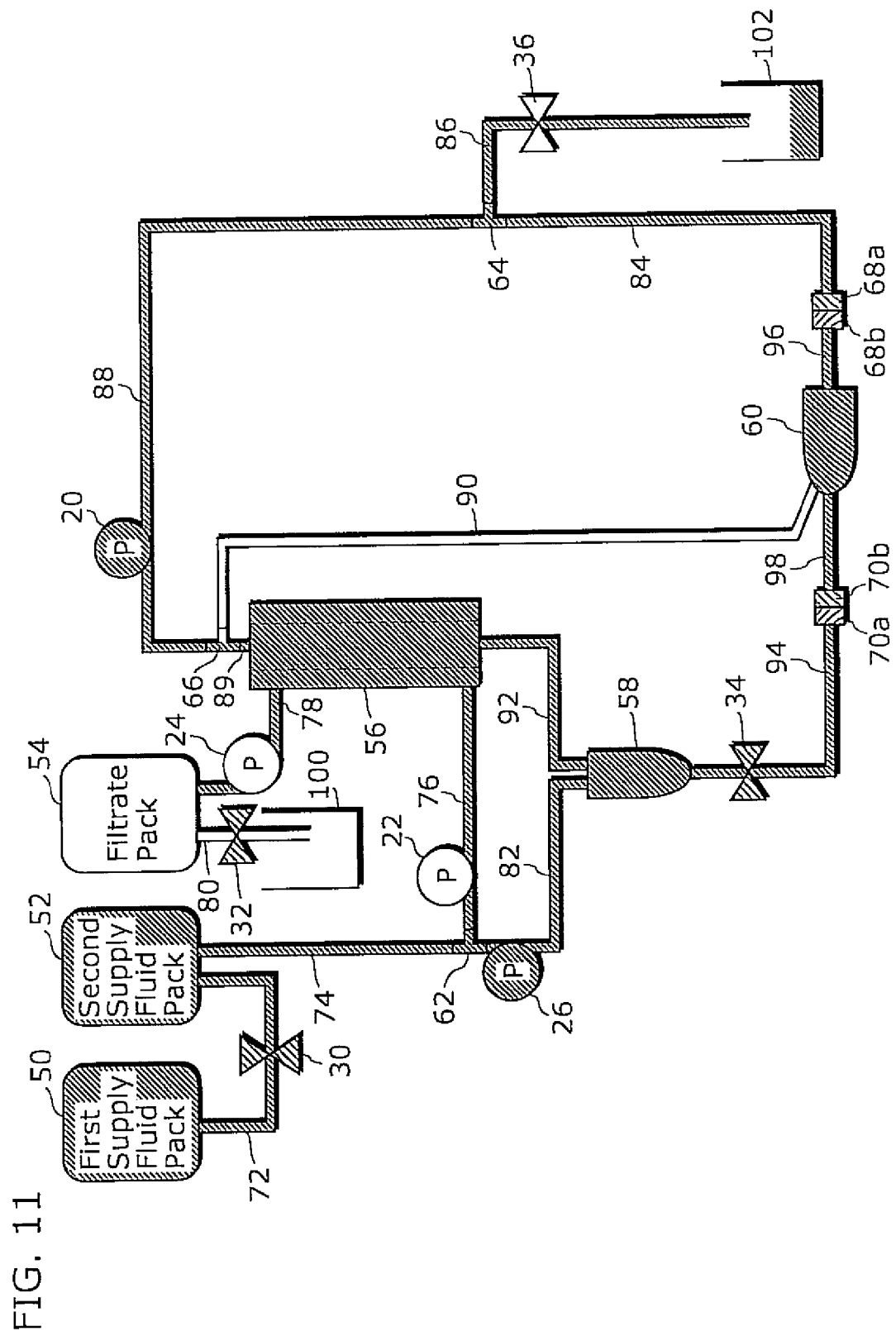
FIG. 11 is a diagram showing a state 6 in the states of the priming of the blood purification circuit according to the first embodiment of the present invention.

The control unit 49 activates the blood pump 20 in a direction opposite to the direction of the blood purification to remove all air from the blood return chamber 58, and closes the blood return valve 34 when all air has been removed from the blood return chamber 58 and the second blood removal line 88 has been filled with the fluid (S6). Thereby, the state of the blood purification circuit becomes the state 6 in FIG. 5 in which the blood return chamber 58, the first blood return line 92, the inside of the hollow fibers in the hemofilter 56 (serving as a part of the blood circuit), the third blood removal line 89, and the second blood removal line 88 are filled with the fluid. The state 6 of the blood purification circuit is shown in FIG. 11. The control unit 49 that closes the blood return valve 34 and activates the blood pump 20 when the replacement fluid pump 26 is operated corresponds to the "first control unit" in the aspect of the present invention.

This step (process) of closing the blood return valve 34 is a step of closing the blood return line, which corresponds to the "first step" in the aspect of the present invention. Furthermore, the step of activating the blood pump 20 in a direction opposite to the direction of the blood purification is a step of pumping the priming fluid from the hemofilter 56 to the blood removal line, which corresponds to the "third step" in the aspect of the present invention.

As shown in FIG. 11, when the blood return valve 34 connected to the outlet of the blood return chamber 58, the priming fluid entering from the replacement fluid line 82 is stored in the blood return chamber 58 from the bottom to fill the entire chamber. In addition, when the blood return valve 34 arranged as described above is closed, it is possible to run the fluid in the inside of the hollow fibers in the hemofilter 56 in an opposite direction.

Furthermore, the blood pump 20 adjusts an amount of the fluid flowing in the third blood removal line 89, and the replacement fluid pump 26 adjusts an amount of the fluid flowing in the first blood return line 92. If the amount of the fluid flowing in the third blood removal line 89 is equal to the amount of the fluid flowing in the first blood return line 92, it is possible to suppress a pressure on the fluid flowing in the inside of the hollow fibers in the hemofilter 56. However, in fact, errors or irregularity of the pressure of the pumps make it difficult to control the amounts merely by controlling the pumps. Therefore, when there is not the anticoagulant (bypass) line 90, a difference between the amount of the fluid flowing in the third blood removal line 89 and the amount of the fluid flowing in the first blood return line 92 causes an excessive pressure on the hemofilter 56. The anticoagulant (bypass) line 90 enables such an excessive pressure to flee.

Therefore, the anticoagulant (bypass) line 90 serving as a bypass line of the fluid can reduce a pressure on the hemofilter 56. As a result, it is possible to more surely perform priming for the inside of the hollow fibers in the hemofilter 56 (serving as a part of the blood circuit).

Next, the description is given referring back to FIG. 4.

Figure 12:
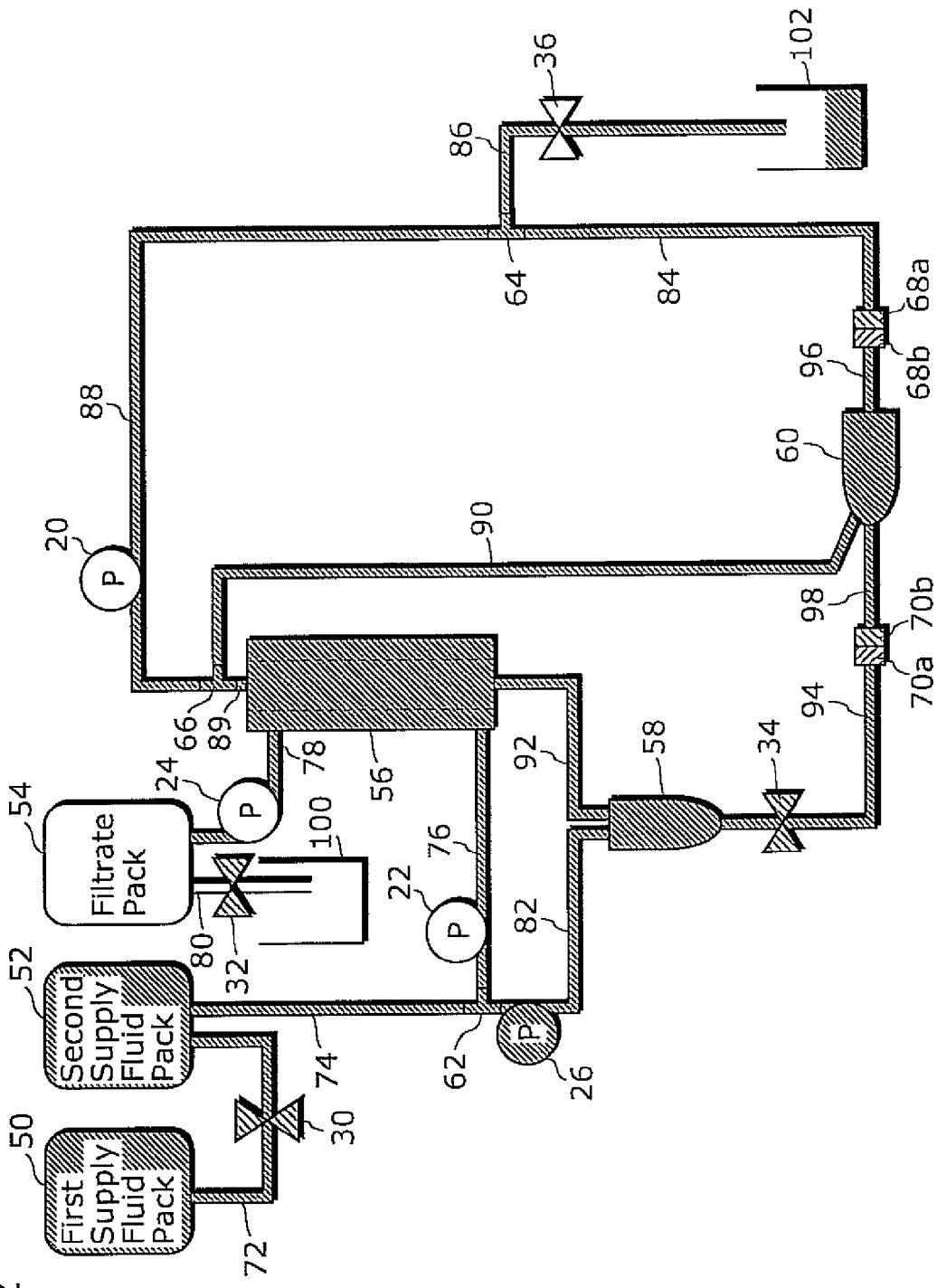
FIG. 12 is a diagram showing a state 7 in the states of the priming of the blood purification circuit according to the first embodiment of the present invention.

After discharging the fluid to the waste fluid tank 102, the control unit 49 stops the blood pump 20 (S7). Thereby, the state of the blood purification circuit becomes the state 7 in FIG. 5 in which the anticoagulant (bypass) line 90 is filled with the fluid. In other words, priming for the anticoagulant (bypass) line 90 is surely performed. The state 7 of the blood purification circuit is shown in FIG. 12.

By the above steps, the entire blood circuit is filled with the priming fluid. Next, priming starts for the filtrate pack 54 for which priming has not yet been done among the supply fluid circuit.

Figure 13:
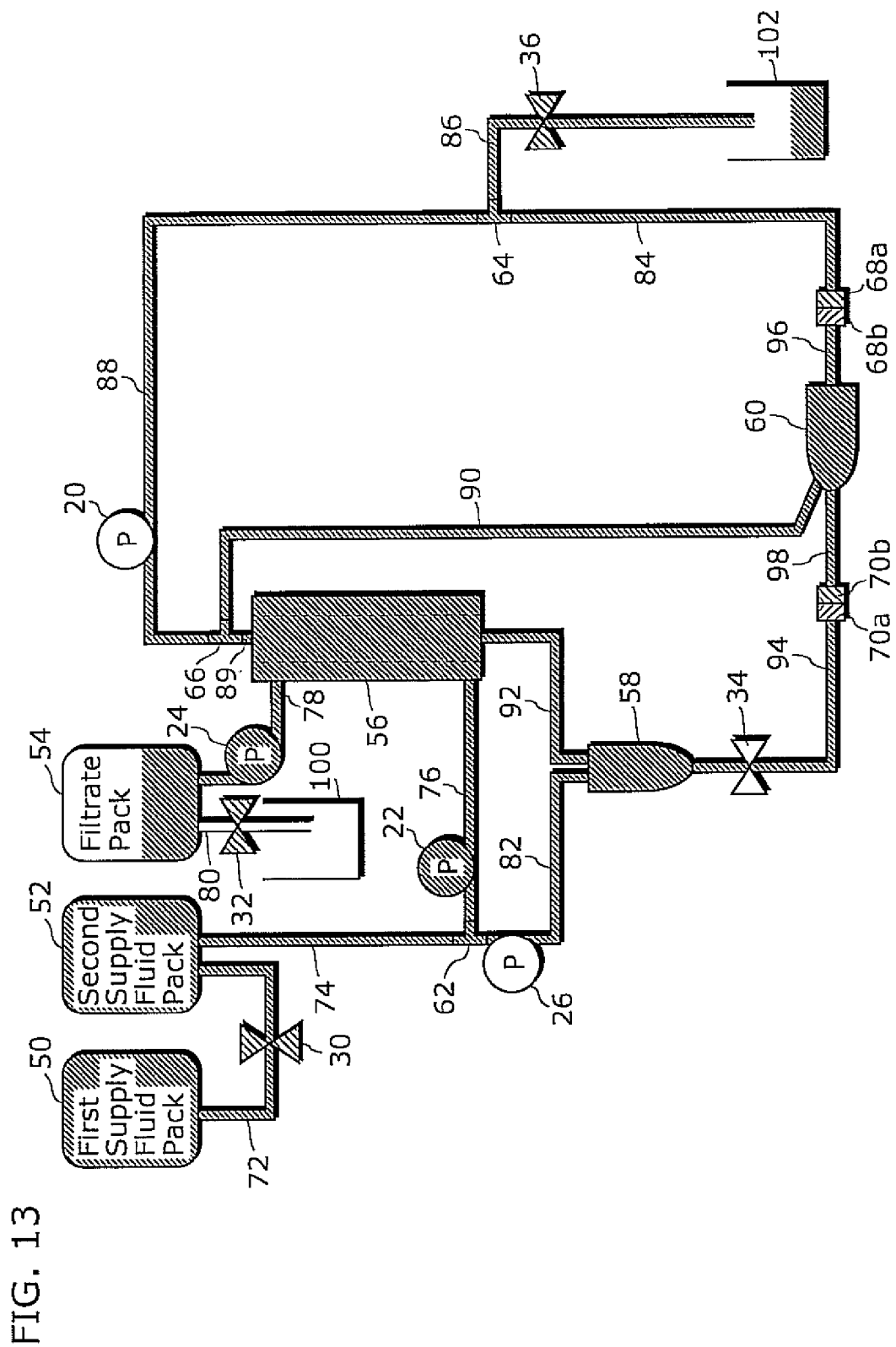
FIG. 13 is a diagram showing a state 8 in the states of the priming of the blood purification circuit according to the first embodiment of the present invention.

The control unit 49 stops the replacement fluid pump 26, activates the dialysis pump 22 and the filtrate pump 24, opens the blood return valve 34, and closes the priming fluid discharge valve 36 (S8). Thereby, the state of the blood purification circuit becomes the state 8 as shown in FIG. 13 in which the fluid is accumulated in the filtrate pack 54. This step (process) of activating the filtrate pump 24 is a step of pumping the priming fluid from the hemofilter 56 via the dialysate outlet of the hemofilter 56 to the filtrate pack 54, which corresponds to the "eighth step" in the aspect of the present invention.

The above steps fill the entire blood purification circuit with the priming fluid.

Figure 14:
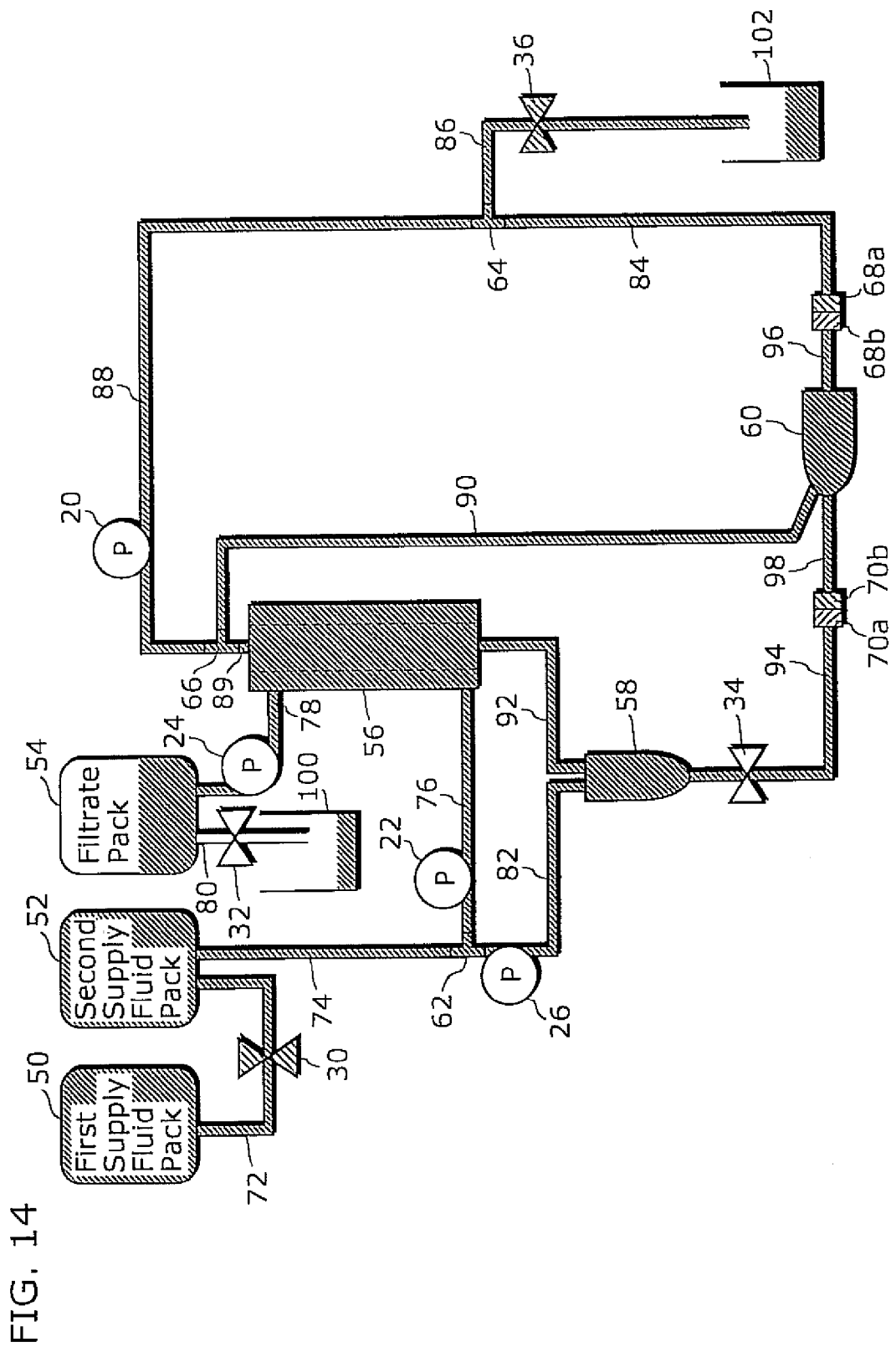
FIG. 14 is a diagram showing a state 9 in the states of the priming of the blood purification circuit according to the first embodiment of the present invention.

The control unit 49 stops the dialysis pump 22 and the filtrate pump 24 and opens the filtrate valve 32 (S9). Thereby, the state of the blood purification circuit becomes the state 9 as shown in FIG. 14 in which a part of the fluid accumulated in the filtrate pack 54 is discharged to the waste fluid tank 100. The control unit 49 that opens the filtrate valve 32 to discharge the part of the fluid accumulated in the filtrate pack 54 corresponds to the "fourth control unit" in the aspect of the present invention. This step (process) of opening the filtrate valve 32 corresponds to the "ninth step" in the aspect of the present invention.

In performing the treatment, the blood purification control apparatus 10 measures an amount of purified blood based on the weight of the second supply fluid pack and the weight of the filtrate pack 54. As described above, by discharging a part of the fluid in the filtrate pack 54, balance between a weight of the second supply fluid pack 52 and a weight of the filtrate pack 54 is adjusted, which makes it possible to more accurately measure an amount of blood purification during the treatment.

As described above, in a series of processes, the blood purification circuit according to the first embodiment can fill a priming fluid not only in the blood circuit and the circulation circuit but also in the supply fluid circuit. Furthermore, since the balance between the weight of the second supply fluid pack 52 and the weight of the filtrate pack 54 is adjusted in the series of processes, it is possible to perform preparation for safe treatment without imposing operation loads on the operator performing the preparation.

The control unit 49 activates the blood pump 20 (S10). Thereby, by circulating the priming fluid in the blood circuit, recirculation is performed to remove air remaining in the blood circuit.

Figure 15:
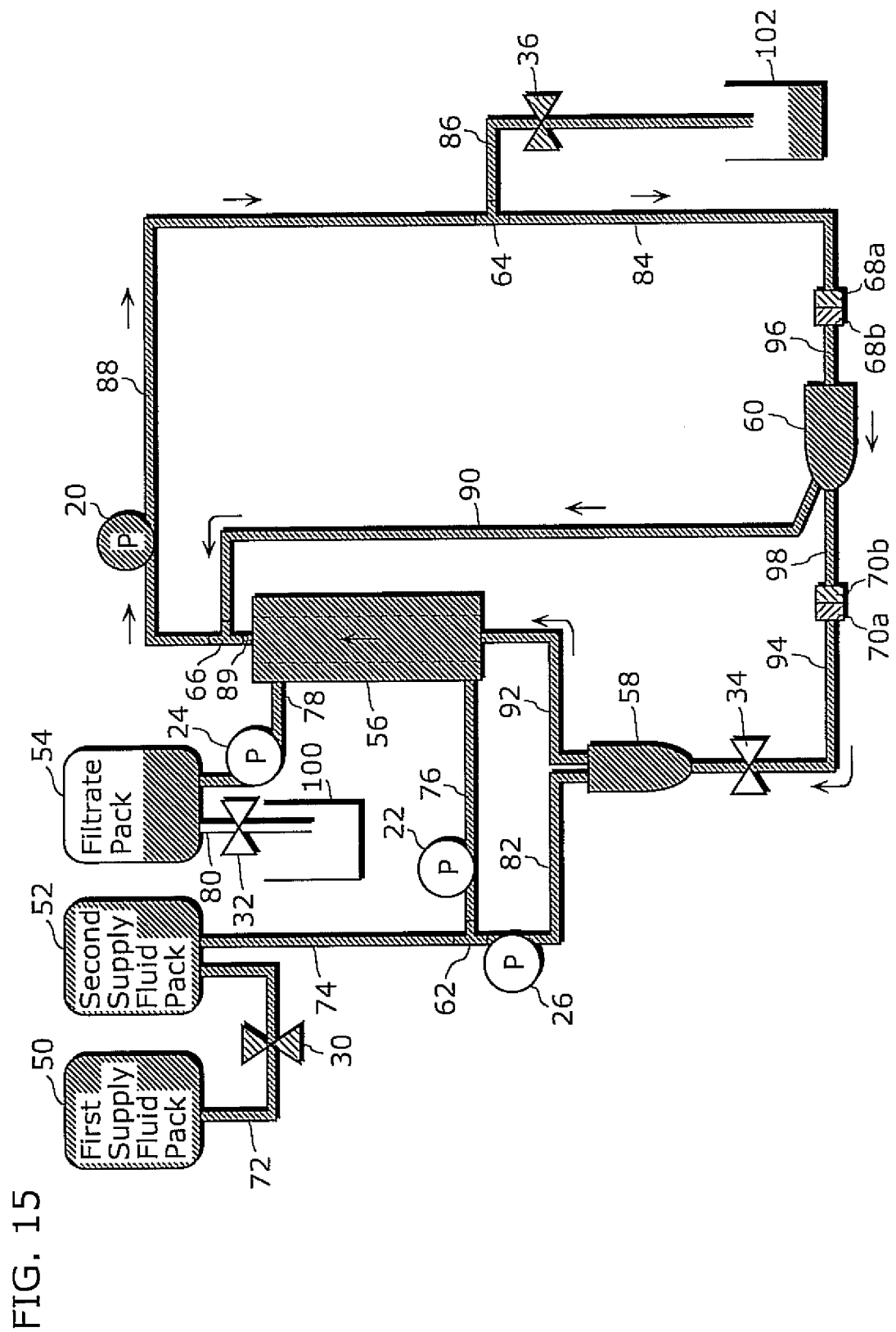
FIG. 15 is a diagram of a flow of a priming fluid in a blood circuit in performing recirculation according to the first embodiment of the present invention.

FIG. 15 is a diagram of a flow of a priming fluid in the blood circuit in performing the recirculation according to the first embodiment. As shown in FIG. 15, by circulating the priming fluid in the blood circuit according to the first embodiment, the air remaining in the blood circuit is trapped in the recirculation chamber 60. Such recirculation continues until the treatment starts. As described above, the control unit 49 that activates the blood pump 20 to control the recirculation corresponds the "recirculation control unit" in the aspect of the present invention. The recirculation is a step (process) of circulating the priming fluid in the circularly-arranged circuit and corresponds to the "fifth step" in the aspect of the present invention.

The blood purification circuit according to the first embodiment includes the recirculation chamber in the circulation circuit in which the blood circuit serves as a circulation structure for priming. By performing the recirculation (namely, circulation of the priming fluid in the blood circuit) when the above-described blood purification circuit is set, air remaining in the blood circuit even after priming can be captured and collected in the recirculation chamber. When the treatment is to be performed, the circulation circuit including the recirculation chamber is removed from the blood circuit and then discarded. Thereby, the air collected in the recirculation chamber is discarded together with the circulation circuit.

Merely providing the recirculation chamber in the circulation circuit can remove air remaining in the blood circuit, and it is not necessary to add a new process in the series of blood purification processes having the priming and the treatment. Therefore, it is possible to more surely remove air from the blood circuit without imposing loads on the operator.

The above has described one of embodiments of the present invention, and the present invention is not limited to the above.

For example, in the first embodiment, since the anticoagulant (bypass) line 90 serving as a bypass line reduces a pressure on the hemofilter 56, the anticoagulant branch part 66 located between the blood inlet of the hemofilter 56 and the blood pump 20 is connected to the outlet of the recirculation chamber 60, as an example of the line for reducing a difference between (a) a pressure of the priming fluid flowing in the blood removal line and (b) a pressure of the priming fluid flowing in the blood return line.

A pressure on the hemofilter 56 can be reduced when the pressure on the hemofilter 56 produced by the blood pump 20 and the replacement fluid pump 26 flees from one end of the bypass line to other line. However, the bypass line needs to be provided so that air does not flow back in performing the recirculation.

The circularly-arranged circuit consisting of the blood circuit and the circulation circuit is branched to a line with a high pressure connected to the replacement fluid line 82 and a line with a low pressure connected to the rapid replacement fluid line, by the blood return valve 34 and the blood pump 20. The bypass line is connected to such a line with a high pressure and a line with a low pressure.

In other words, the line for reducing a difference between a pressure of the priming fluid flowing in the blood removal line and a pressure of the priming fluid flowing in the blood return line is a line having: (a) one end connected to (a1) a position between the blood pump attachment part and the blood inlet of the hemofilter 56, (a2) a position between the blood outlet of the hemofilter 56 and the blood return valve attachment part (including the blood return chamber 58), or (a3) a position between the replacement fluid pump 26 and the blood return chamber 58; and (b) the other end connected to (b1) a position in a line located upstream of the blood pump 20 in the blood removal line or (b2) a position in a line located downstream of the blood return valve 34 of the blood return line.

In more detail, there is a case (hereinafter, referred to as a "first case") where one end of the bypass line is connected to (a1) a position between the blood pump attachment part and the blood inlet of the hemofilter 56, and the other end of the bypass line is connected to (b1) a position between the blood pump attachment part and the blood removal side joint 68a, (b2) a position in the circulation line, (b3) a position between the blood return valve attachment part and the blood return side joint 70a, or (b4) a position in the priming fluid discharge (rapid replacement fluid) line 86. The first embodiment provides an example where the other end is connected to a position in the circulation line in the above first case.

There is another case (hereinafter, referred to as a "second case") where one end of the bypass line is connected to (a2) a position between the blood outlet of the hemofilter 56 and the blood return valve attachment part (including the blood return chamber 58), and the other end of the bypass line is connected to (b1) a position between the blood pump attachment part and the blood removal side joint 68a, (b2) a position in the circulation line, (b3) a position between the blood return valve attachment part and the blood return side joint 70a, or (b4) a position in the priming fluid discharge (rapid replacement fluid) line 86.

Figure 16:
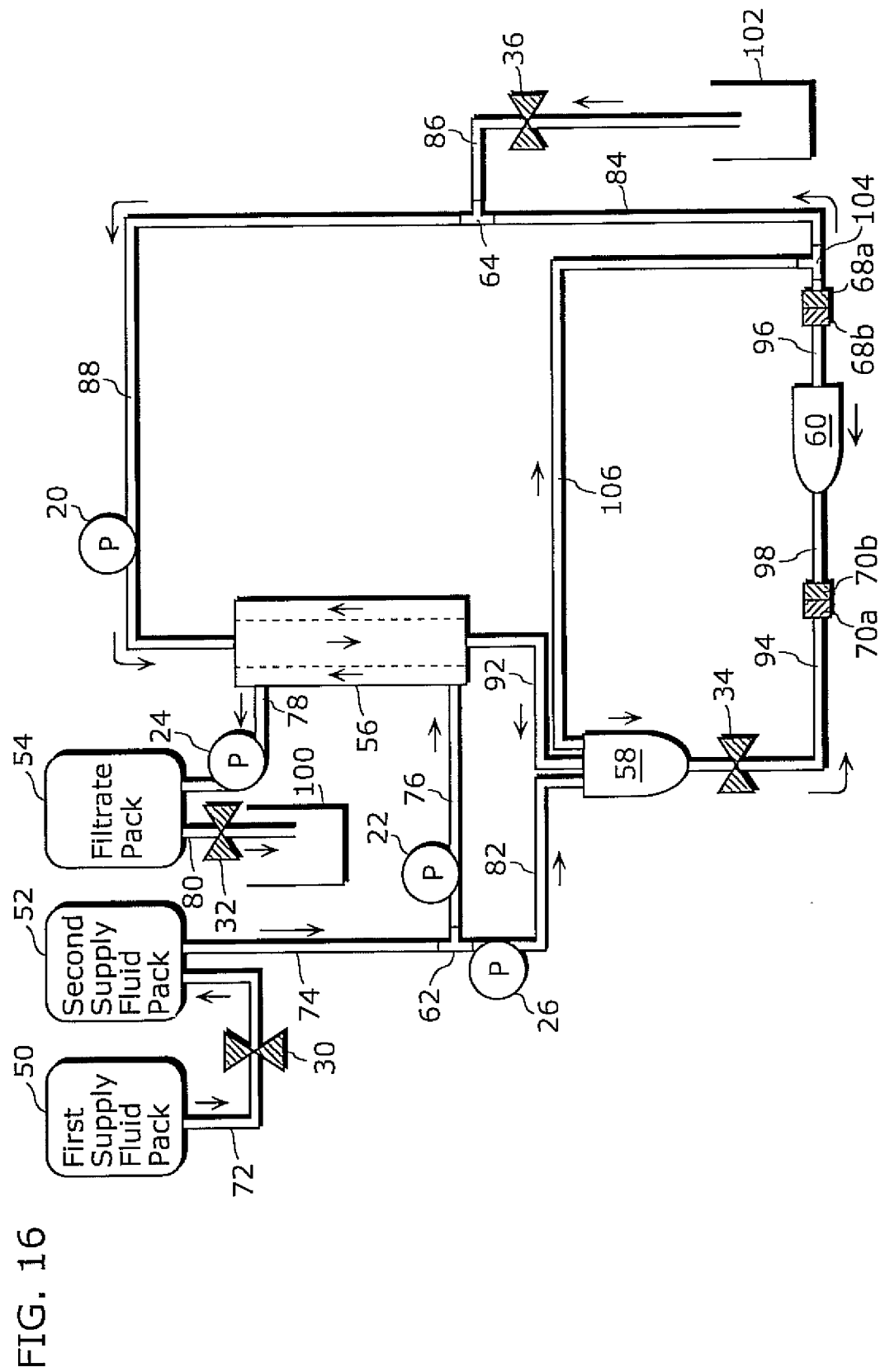
FIG. 16 is a simplified diagram showing a structure of a blood purification circuit in performing priming and position relationships with pumps, valves, and pressure sensors of a blood purification control apparatus, according to a variation of the first embodiment of the present invention.

For example, FIG. 16 is a diagram showing a structure of a blood purification circuit according to a variation of the first embodiment of the present invention. The anticoagulant (bypass) line 106 shown in FIG. 16 connects the inlet of the blood return chamber 58 with the first blood removal line 84. The variation is an example where the other end of the bypass line is connected to a position between the blood pump arrangement part and the blood removal side joint 68a in the above second case.

There is still another case (hereinafter, referred to as a "third case") where one end of the bypass line is connected to (a3) a position between the replacement fluid pump 26 and the blood return chamber 58, and the other end of the bypass line is connected to (b1) a position between the blood pump attachment part and the blood removal side joint 68a, (b2) a position in the circulation line, (b3) a position between the blood return valve attachment part and the blood return side joint 70a, or (b4) a position in the priming fluid discharge (rapid replacement fluid) line 86.

Since this bypass line can serve also as a line for administering an anticoagulant in performing the treatment, an end of the bypass line can be selected as a position from which the anticoagulant is to be administered. The above-described circuit structure can also automatically perform priming in a series of control processes, without attaching and removing a pack storing a priming fluid for the treatment.

A position in a line which is connected to the other end of the bypass line is preferably where the other end is easily disconnected from the line, or is far from the outlet of the priming fluid discharge (rapid replacement fluid) line 86.

An example of the position where the other end of the bypass line is easily disconnected from the line is a chamber. The other end of the bypass line is disconnected from the line, to be connected to the anticoagulant injection device after the priming and the recirculation. Therefore, if the bypass line is connected to the position where the other end of the bypass line is easily disconnected from the line, the processing until the treatment can be simplified.

On the other hand, examples of the position far from the open end (outlet) of the priming fluid discharge (rapid replacement fluid) line 86 are (a1) a position in the blood circuit except the priming fluid discharge (rapid replacement fluid) line 86 (namely, a position between the blood pump attachment part and the blood removal side joint 68a), (a2) a position in the middle of the circulation line, and (a3) a position between the blood return valve attachment part and the blood return side joint 70a.

In performing priming, the priming fluid which has passed the bypass line flows in a part of the blood circuit and then in the priming fluid discharge (rapid replacement fluid) line 86, and eventually is discharged from the blood purification circuit. Therefore, the priming fluid which has passed the bypass line is used in priming for a line from (a) a position where the blood circuit is connected to the bypass line to (b) the open end of the priming fluid discharge (rapid replacement fluid) line 86. As a result, when the position in a line which is connected to the other end of the bypass line is arranged far from the open end of the priming fluid discharge (rapid replacement fluid) line 86, the priming fluid can be used to perform priming for a longer line, thereby utilizing the priming fluid efficiently.

Second Embodiment

The blood purification control apparatus according to the second embodiment basically has the same functions (structure elements) as those of the blood purification control apparatus 10 according to the first embodiment shown in FIG. 1. The blood purification control apparatus according to the second embodiment controls priming and blood purification for a patient, using the blood circuit having the same circuit structure as that of the first embodiment shown in FIGS. 2 and 3.

The blood purification control apparatus according to the second embodiment differs from the blood purification control apparatus 10 according to the first embodiment in a content of the automatic priming mode information 48a stored in the control method storage unit 48 (namely, control processing to be performed in the priming by the control unit 49 included in the blood purification control apparatus 10). The processing of priming performed by the blood purification control apparatus 10 according to the second embodiment is described with reference to FIGS. 17 and 26. It should be noted that, in the blood purification control apparatus 10 according to the second embodiment, the anticoagulant (bypass) line 90 has a check valve 37 as shown in FIGS. 19 to 26.

FIG. 17 is a flowchart of processes of automatic priming performed by the blood purification control apparatus 10 when an automatic priming mode is selected, according to the second embodiment.

FIG. 17 shows processing performed by the control unit 49 to control each pump and each valve of the blood purification control apparatus 10, when the mode receiving unit 16 receives the selection of the automatic priming mode inputted by the operator using the input unit 12 and the control unit 49 reads out the automatic priming mode information 48a from the control method storage unit 48 and performs the automatic priming mode based on the readout automatic priming mode information 48a.

FIG. 18 is a table of statues of the blood purification circuit in the respective processes of the priming according to the second embodiment. Each of FIGS. 19 to 26 is a diagram showing a corresponding state in the states of the priming of the blood purification circuit.

The following describes the processes (steps) shown in FIG. 17 and a state of the blood purification circuit corresponding to each of the processes with reference to FIGS. 18 to 26.

Figure 19:
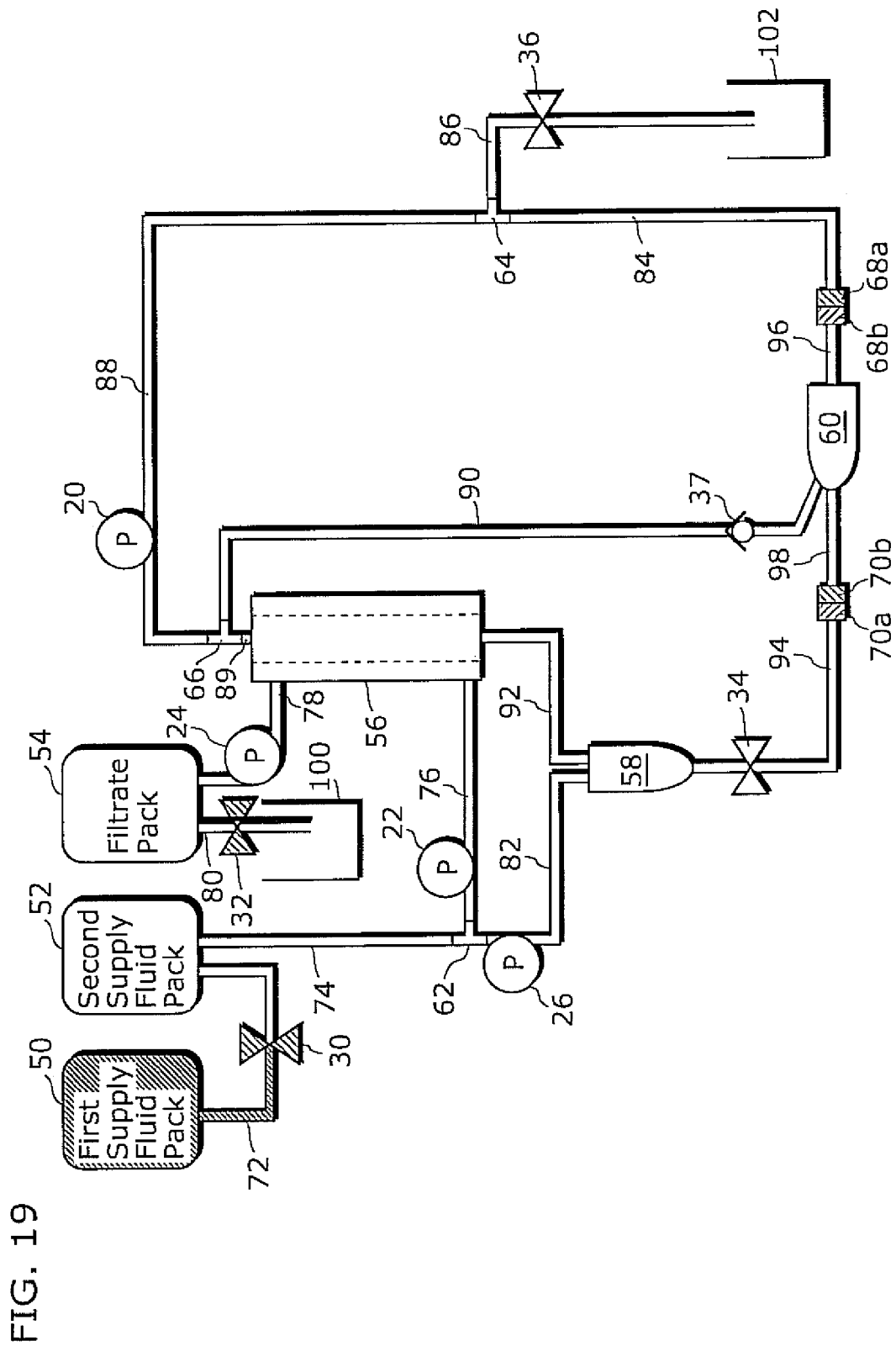
FIG. 19 is a diagram showing a state 1 in the states of the priming of the blood purification circuit according to the second embodiment of the present invention.

In the initial state, it is assumed that the blood purification control apparatus 10 is provided with the blood purification circuit in the manner as shown in FIGS. 2 and 3, and that a priming fluid is stored only in the first supply fluid pack 50. In addition, as shown in the initial state in FIG. 18, it is assumed that all pumps stop, the supply fluid valve 30 and the filtrate valve 32 are closed, and the blood return valve 34 and the priming fluid discharge valve 36 are opened in the blood purification control apparatus 10. The initial state of the blood purification circuit is shown in FIG. 19.

The control unit 49 opens the supply fluid valve 30 (S11). Thereby, the state of the blood purification circuit becomes the state 1 in FIG. 18 in which the first supply fluid line 72 and the second supply fluid pack 52 are filled with the priming fluid (hereinafter in the explanation of the processes of priming, referred to simply as a "fluid"). The state 1 of the blood purification circuit is shown in FIG. 20.

Figure 20:
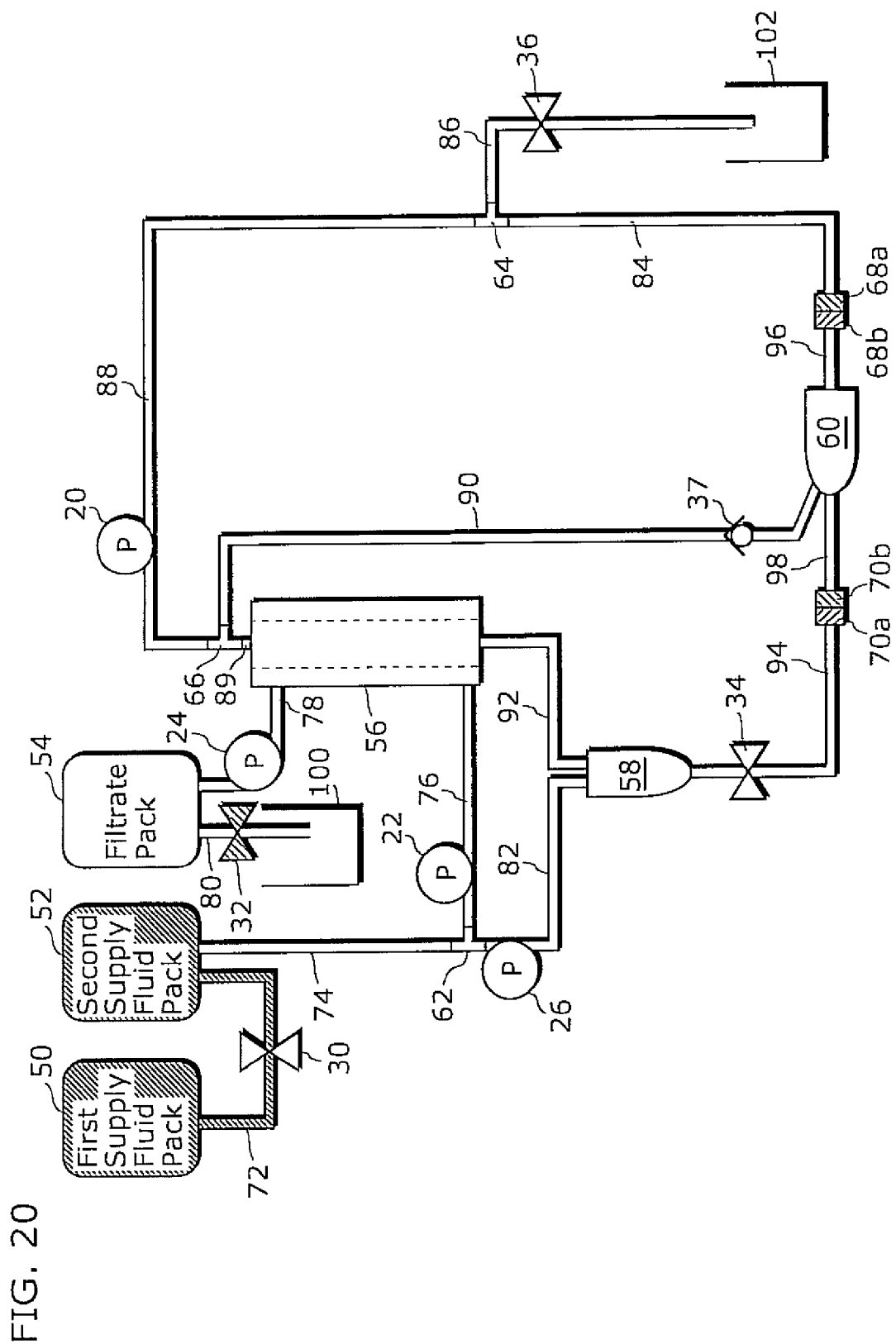
FIG. 20 is a diagram showing a state 2 in the states of the priming of the blood purification circuit according to the second embodiment of the present invention.

FIG. 20 shows the state 1 in the states of the blood purification circuit in performing priming according to the second embodiment. In FIG. 20, a hatched area in the blood purification circuit shows a part where the fluid is filled (namely, the priming has been done). On the other hand, areas not hatched show parts where the fluid has not yet been filled (namely, the priming has no yet been done). In addition, in FIG. 20, a hatched valve shows a closed valve, and valves not hatched show open valves.

The hatching in the blood purification circuit and the valve in FIG. 20 shows the above-described situations also in FIGS. 21 to 26. Therefore, the explanation of the hatching in FIGS. 21 to 26 is not given again below.

Furthermore, in FIG. 20, all pumps are not shown hatched. This means that all pumps stop. Likewise, each pump that stops is not shown hatched and each pump that is activated is shown hatched in FIGS. 21 to 26. The hatching in pumps is explained above, so that it is not explained again for each figure.

Now, the description is given referring back to FIG. 17.

Figure 21:
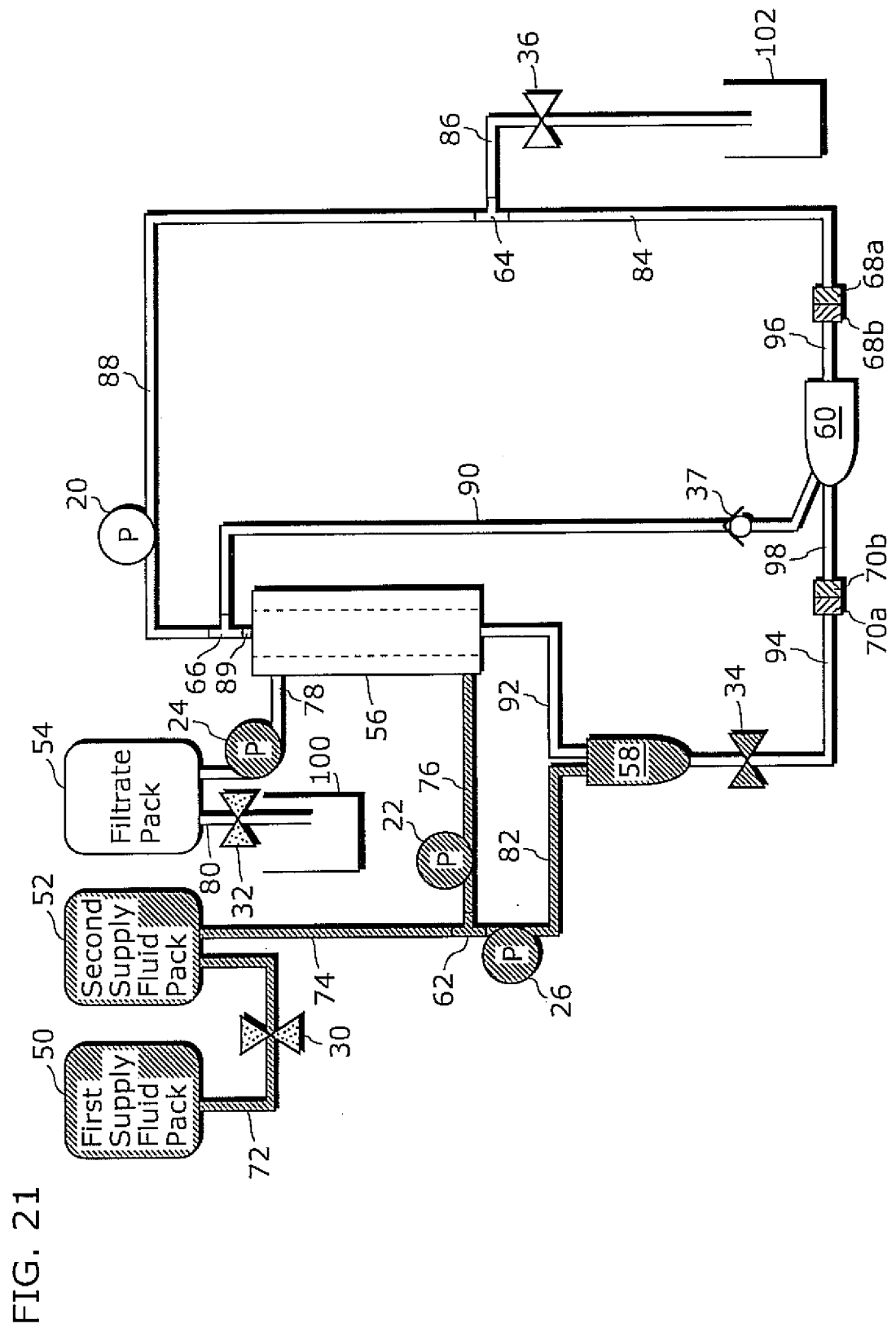
FIG. 21 is a diagram showing a state 2 in the states of the priming of the blood purification circuit according to the second embodiment of the present invention.

The control unit 49 activates the dialysis pump 22 to operate at 20 ml/second, the filtrate pump 24 to operate at 20 ml/second, the replacement fluid pump 26 to operate at 60 ml/second, and closes the blood return valve 34 (S12). Thereby, the state of the blood purification circuit becomes the state 2 in FIG. 18 in which the second supply fluid line 74, the dialysate line 76, and the replacement fluid line 82 are filled with the fluid. Then, filling of the fluid in the blood return chamber 58 starts. The state 2 of the blood purification circuit is shown in FIG. 21. The control unit 49 that closes the blood return valve 34 and activates the replacement fluid pump 26 corresponds to the "first control unit" in the aspect of the present invention.

After the step (process), each of the supply fluid valve 30 and the filtrate valve 32 is independently controlled based on a measurement result of the measurement sensors. In FIG. 18, opening and closing of the supply fluid valve 30 and the filtrate valve 32 in the states 2 to 7 are indicated as "*", which means that each of the supply fluid valve 30 and the filtrate valve 32 is independently controlled. In FIGS. 22 to 26 showing the states of the blood purification circuit, each of the supply fluid valve 30 and the filtrate valve 32 is shown with dots, showing that each of them is independently controlled.

Figure 22:
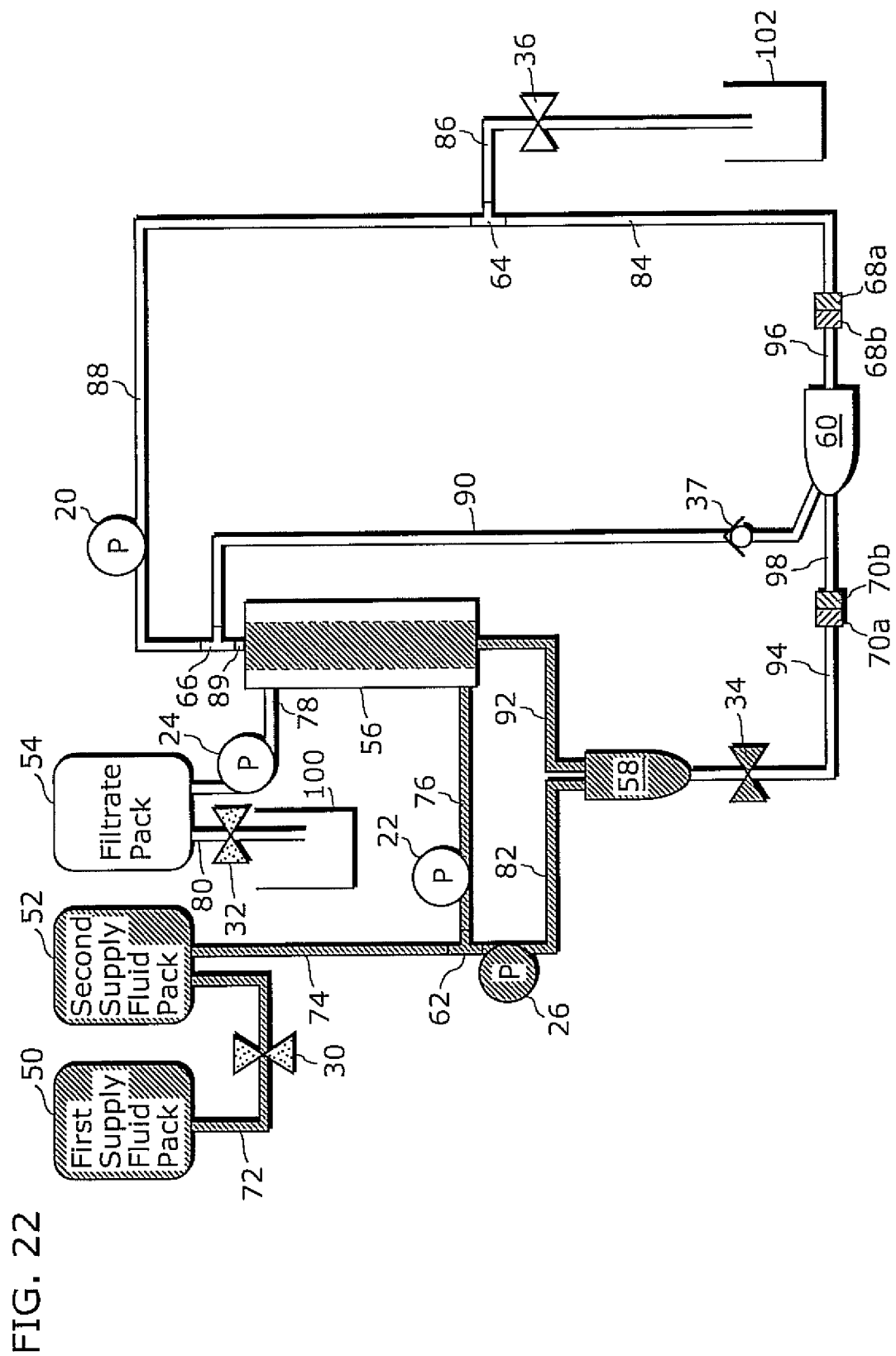
FIG. 22 is a diagram showing a state 3 in the states of the priming of the blood purification circuit according to the second embodiment of the present invention.

The control unit 49 stops the dialysis pump 22 and the filtrate pump 24 (S13). Here, the replacement fluid pump 26 has been operated since the state 2, but its pumping power is reduced to 20 ml/second. Thereby, the state of the blood purification circuit becomes the state 3 in FIG. 18 in which the first blood return line 92, the inside of the hollow fibers of the hemofilter 56 (serving as a part of the blood circuit), and the blood return chamber 58 are filled with the fluid. The state 3 of the blood purification circuit is shown in FIG. 22. The control unit 49 that closes the blood return valve 34 and activates the replacement fluid pump 26 corresponds to the "first control unit" in the aspect of the present invention, likewise the control unit 49 performing control at S12.

Figure 23:
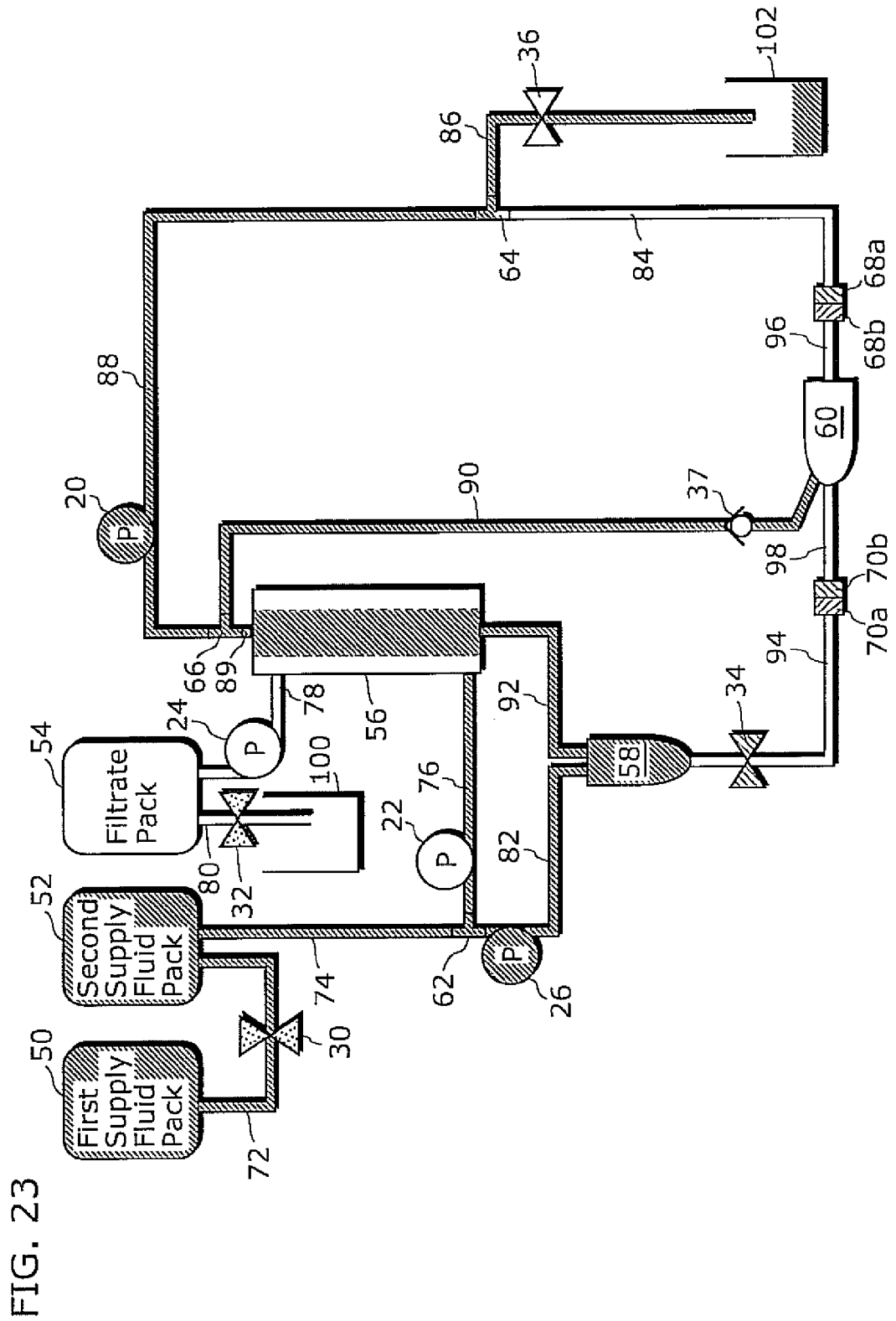
FIG. 23 is a diagram showing a state 4 in the states of the priming of the blood purification circuit according to the second embodiment of the present invention.

The control unit 49 activates the blood pump 20 to operate at 100 ml/second (S14). Here, the replacement fluid pump 26 has been operated since the state 3, but its pumping power is increased to 130 ml/second. Thereby, the state of the blood purification circuit becomes the state 4 in FIG. 18 in which the third blood removal line 89, the second blood removal line 88, the priming fluid discharge (rapid replacement fluid) line 86, and the anticoagulant (bypass) line 90 are filled with the fluid. The state 4 of the blood purification circuit is shown in FIG. 23. The control unit 49 that closes the blood return valve 34 and activates the replacement fluid pump 26 and the blood pump 20 corresponds to the "first control unit" in the aspect of the present invention.

Here, an amount of a fluid pumped by the replacement fluid pump 26 is greater than an amount of a fluid pumped by the blood pump 20. The replacement fluid pump 26 adjusts an amount of a fluid in the first blood return line 92, and the blood pump 20 adjusts an amount of a fluid in the second blood removal line 88. A pressure on the inside of the hollow fibers in the hemofilter 56 (serving as a part of the blood circuit) is adjusted by the two pumps. As a result, it is possible to surely fill a priming fluid in the inside of the hollow fibers in the hemofilter 56.

In addition, the anticoagulant (bypass) line 90 has a check valve 37 by which a fluid can run only in a direction from the hemofilter 56 to the recirculation chamber 60. With the check valve 37, it is possible to prevent that air enters the anticoagulant (bypass) line 90 from the recirculation chamber 60.

The control unit 49 activates the dialysis pump 22 to operate at 140 ml/second and the filtrate pump 24 to operate at 110 ml/second, and opens the blood return valve 34 (S15). Here, the blood pump 20 has been operated since the state 4, but its pumping power is increased to 110 ml/second. The replacement fluid pump 26 has been operated since the state 4, but it pumping power is increased to 140 ml/second.

Figure 24:
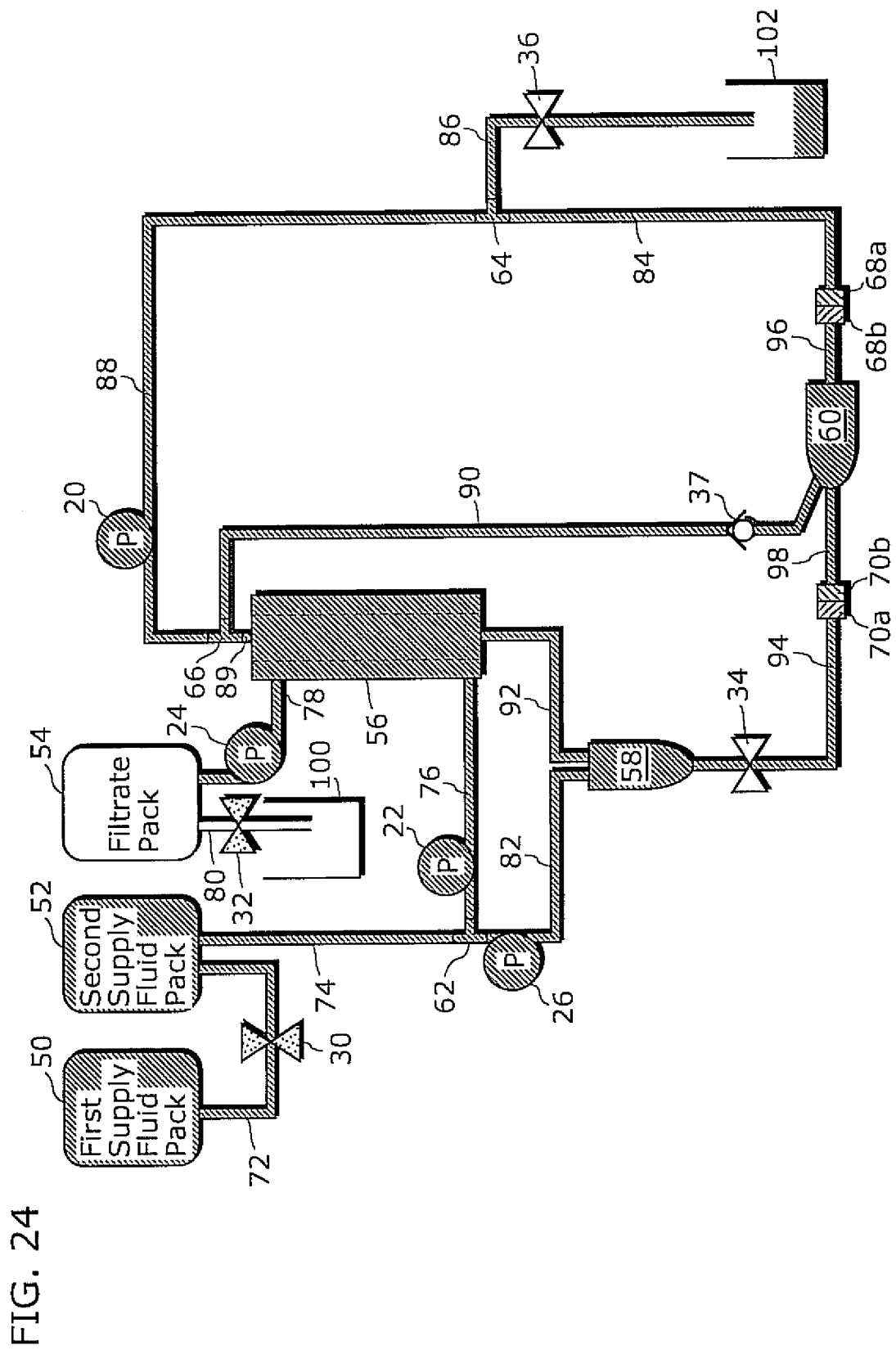
FIG. 24 is a diagram showing a state 5 in the states of the priming of the blood purification circuit according to the second embodiment of the present invention.

Thereby, the state of the blood purification circuit becomes the state 5 in FIG. 18 in which the second blood return line 94, the first circulation line 96, the recirculation chamber 60, the second circulation line 98, the first blood removal line 84, the outside of the hollow fibers in the hemofilter 56 (serving as a part of the supply fluid circuit), and the filtrate line 78 is filled with the fluid. The state 5 of the blood purification circuit is shown in FIG. 24.

The control unit 49 that activates the replacement fluid pump 26 when the blood return valve 34 is opened corresponds to the "second control unit" in the aspect of the present invention.

Each of the control unit 49 that activates the dialysis pump 22, and the control unit 49 that activates the dialysis pump 22 and the filtrate pump 24 corresponds to the "third control unit" in the aspect of the present invention.

When the dialysis pump 22 and the filtrate pump 24 are operated together to perform priming for the outside of the hollow fibers in the hemofilter 56, an amount of a fluid pumped by the dialysis pump 22 is greater than an amount of a fluid pumped by the filtrate pump 24. The dialysis pump 22 adjusts an amount of a fluid entering the outside of the hollow fibers in the hemofilter 56, and the filtrate pump 24 adjusts an amount of a fluid exiting from the outside of the hollow fibers in the hemofilter 56. Since the dialysis pump 22 pumps a fluid more than a fluid pumped by the filtrate pump 24, it is possible to keep the situation where a positive pressure is applied on the outside of the hollow fibers in the hemofilter 56. Therefore, air does not enter the outside of the hollow fibers in the hemofilter 56 via the filtrate line 78. When the blood return valve 34 is opened, the fluid runs in a direction from the blood return chamber 58 to the second blood return line 94, which reduces a pressure on the first blood return line 92 and a pressure on the inside of the hollow fibers in the hemofilter 56. Thereby, the pressure on the outside of the hollow fibers is higher than the inside of the hollow fibers in the hemofilter 56, so that he fluid in the outside of the hollow fibers enters the inside of the hollow fibers. Here, since the fluid enters the hollow fiber film between the outside and the inside of the hollow fibers in the hemofilter 56, air can be removed from the hollow fiber film. The removal of the air from the hemofilter 56 makes it possible to surely perform priming for the hemofilter 56.

The control unit 49 stops the blood pump 20 and the replacement fluid pump 26 (S16). Here, the dialysis pump 22 has been operated since the state 5, but its pumping power is decreased to 130 ml/second. The filtrate pump 24 has been operated since the state 5, but its pumping power is decreased to 100 ml/second. Thereby, the state of the blood purification circuit becomes the state 6 in FIG. 18 in which the outside of the hollow fibers in the hemofilter 56 and the filtrate line 78 are completely filled with the fluid, and the fluid is accumulated in the filtrate pack 54. The state 6 of the blood purification circuit is shown in FIG. 25.

Figure 25:
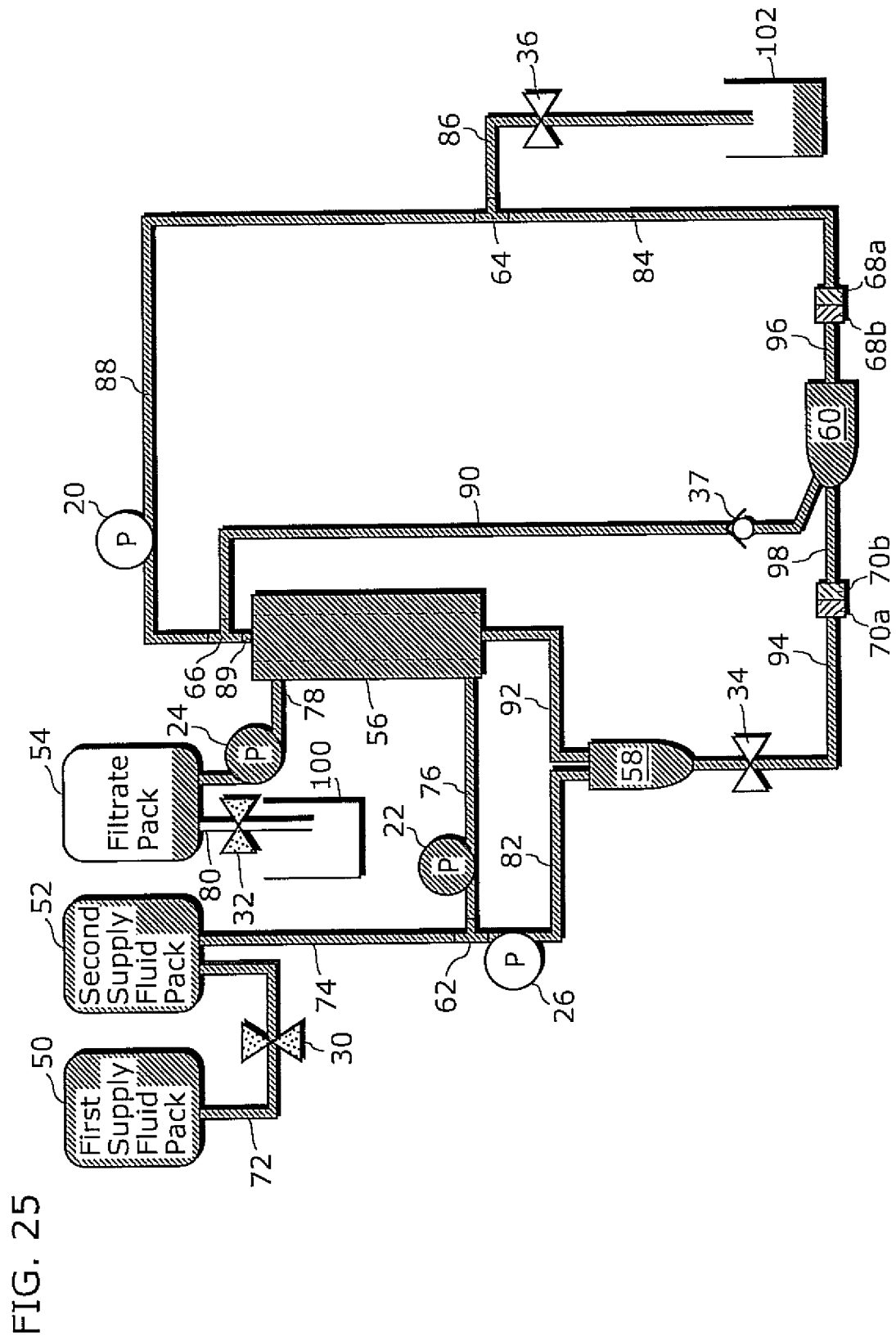
FIG. 25 is a diagram showing a state 6 in the states of the priming of the blood purification circuit according to the second embodiment of the present invention.

As shown in FIG. 25, in the blood purification circuit, the filtrate valve 32 is opened and a part of the fluid accumulated in the filtrate pack 54 is discharged to the waste fluid tank 100. The control unit 49 that opens the filtrate valve 32 to discharge the part of the fluid accumulated in the filtrate pack 54 corresponds to the "fourth control unit" in the aspect of the present invention.

In performing the treatment, the blood purification control apparatus 10 measures an amount of purified blood using a weight of the second supply fluid pack and a weight of the filtrate pack 54. By discharging a part of the fluid accumulated in the filtrate pack 54, it is possible to adjust balance between the weight of the second supply fluid pack 52 and the weight of the filtrate pack 54. As a result, an amount of purified blood can be more accurately measured. With the above-described processing, the priming fluid is filled in the entire blood purification circuit.

The control unit 49 stops the dialysis pump 22 and the filtrate pump 24, activates the blood pump 20 to operate at 100 ml/second, and closes the priming fluid discharge valve 36 (S17). This circulates the priming fluid in the blood circuit, thereby performing recirculation to remove air remaining in the blood circuit.

Figure 26:
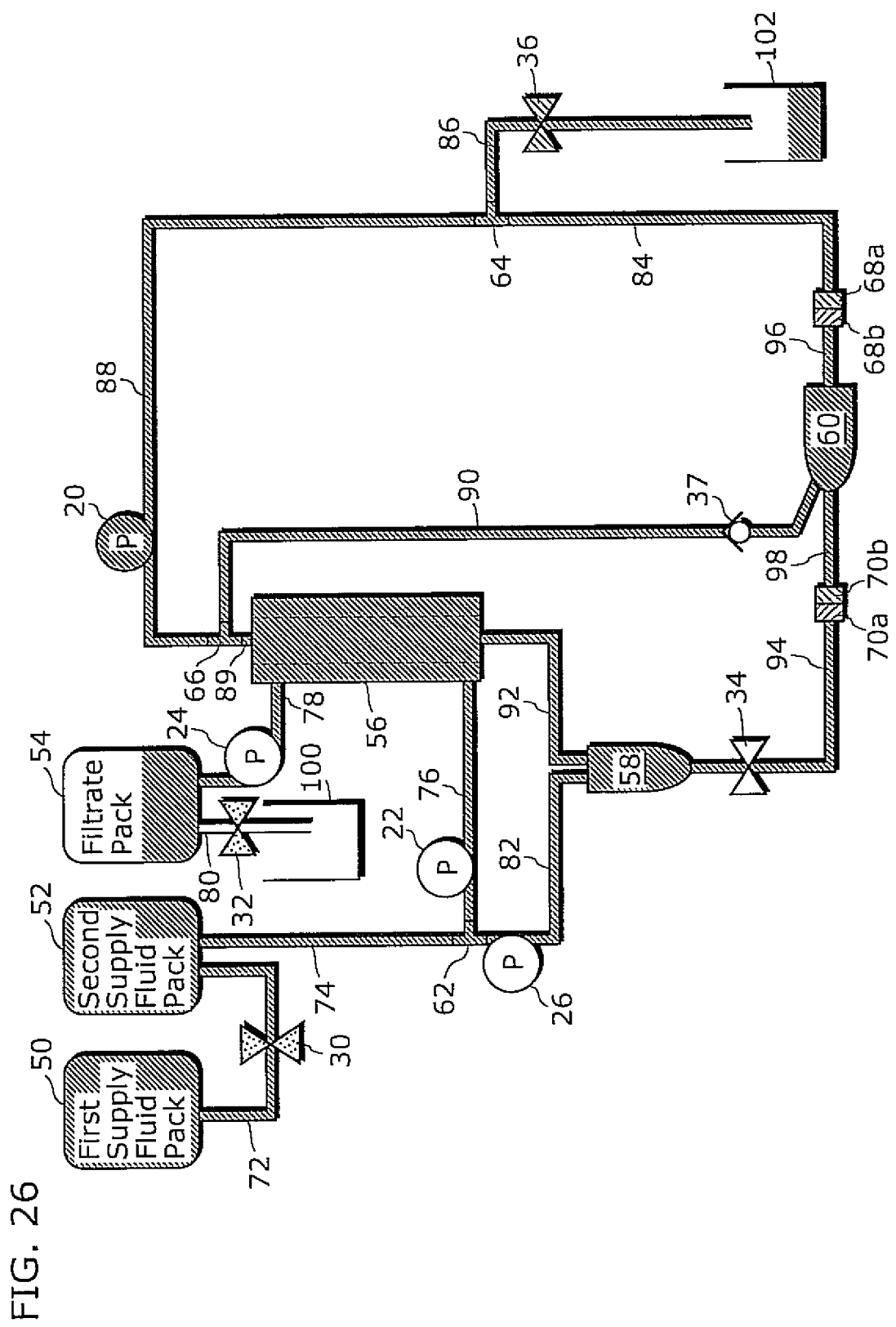
FIG. 26 is a diagram of a flow of a priming fluid in a blood circuit in performing recirculation according to the second embodiment of the present invention.

FIG. 26 is a diagram of a flow of a priming fluid in the blood circuit in performing recirculation according to the second embodiment, likewise FIG. 15 in the first embodiment. As shown in FIG. 26, when a priming fluid circulates in the blood circuit according to the second embodiment, air remaining in the blood circuit is trapped in the recirculation chamber 60. The recirculation continues until the treatment starts. The control unit 49 that activates the blood pump 20 to control recirculation corresponds to the "recirculation control unit" in the aspect of the present invention.

The blood purification circuit according to the embodiment of the present invention has the recirculation chamber in the circulation circuit in which the blood circuit is used as a circulation structure in performing priming. By performing the recirculation (namely, circulation of the priming fluid in the blood circuit) when the above-described blood purification circuit is set, air remaining in the blood circuit even after priming can be captured and collected in the recirculation chamber. Then, each of the blood removal side joint 68a and the blood return side joint 70a in the blood purification circuit is connected to a blood vessel of the patient, and when the blood purification treatment is to be performed, the circulation circuit including the recirculation chamber is removed from the blood circuit and then discarded. Thereby, the air collected in the recirculation chamber is discarded together with the circulation circuit.

Merely providing the recirculation chamber in the circulation circuit can remove air remaining in the blood circuit, and it is not necessary to add a new process in the series of blood purification processes having the priming and the treatment. Therefore, it is possible to more surely remove air from the blood circuit without imposing loads on the operator.

Moreover, it is also necessary to discard the blood circuit after the blood purification treatment is completed. Here, the blood circuit is discarded as still being connected to the circulation circuit including the recirculation chamber, so that fluid leakage can be prevented when discarding the blood circuit and the circulation circuit.

The present invention can be used as a blood circuit, a blood purification control apparatus, and a priming method which are capable of safely and automatically performing priming for purifying blood of a patient.

The invention claimed is:

1. A blood purification control apparatus controlling flow of a fluid in a blood purification circuit that includes a hemofilter purifying blood, a blood removal line connected to a blood inlet of the hemofilter, and a blood return line connected to a blood outlet of the hemofilter, said blood purification control apparatus comprising: a blood return valve for opening and closing the blood return line;
   a first pump provided on a first line to pump a priming fluid to a part between the hemofilter and the blood return valve on the blood return line;
   a first control unit configured to cause the priming fluid to enter the hemofilter from the blood outlet of the hemofilter, by closing the blood return valve and activating the first pump;
   a second pump for (i) pumping the priming fluid to the hemofilter via the blood removal line and (ii) pumping the priming fluid out of the hemofilter via the blood removal line, wherein the first control unit is configured to activate the first pump and the second pump together so that the priming fluid is pumped of the hemofilter;
   a third pump provided on a second line to pump the priming fluid to the hemofilter via a dialysate inlet of the hemofilter; and
   a third line connected to the first line and the second line to supply the priming fluid to the first pump and the third pump.

2. The blood purification control apparatus according to claim 1, wherein the first control unit is configured to control the first pump and the second pump so that a pressure of the priming fluid pumped to by the first pump is higher than a pressure of the priming fluid pumped out by the second pump.

3. The blood purification control apparatus according to claim 1, further comprising a second control unit configured to open the blood return valve and activate the first pump in performing priming.

4. The blood purification control apparatus according to claim 1,
   wherein, in the blood purification circuit, an end of the blood return line is connected via a circulation line to an end of a blood removal line, the end of the blood return line and the end of the blood removal line not being connected to the hemofilter, the blood removal line having another end connected to the blood inlet of the hemofilter, and the circulation line having a chamber, and
   said blood purification control apparatus further comprising:
   a recirculation control unit configured to, after completing priming for the blood purification circuit, open the blood return valve and activate the second pump, so that the priming fluid is recirculated in the hemofilter, the blood removal line, the circulation line, and the blood return line.

5. The blood purification control apparatus according to claim 1, further comprising:
a third control unit configured to activate the third pump in performing priming.

6. The blood purification control apparatus according to claim 5, further comprising:
a fourth pump for pumping the priming fluid out of the hemofilter via a dialysate outlet of the hemofilter,
wherein the third control unit is further configured to activate the fourth pump after a part of the hemofilter is filled with the priming fluid by the third pump, the part serving as a part of a dialysis circuit.

7. The blood purification control apparatus according to claim 6,
wherein the blood purification circuit further includes:
a container in which the priming fluid pumped out of the hemofilter via the dialysate outlet is accumulated;
a dialysate discharge line connecting the dialysate outlet of the hemofilter to the container; and
a discharge line in which the priming fluid accumulated in the container flows to be discharged,
the fourth pump circulates the priming fluid in the dialysate discharge line, and
the blood purification control apparatus further comprising:
a discharge valve for opening and closing the discharge line; and
a fourth control unit configured to (i) close the discharge valve and activate the third pump and the fourth pump to accumulate the priming fluid in the container, and (ii) after the accumulation, open the discharge valve to discharge a part of the priming fluid accumulated in the container.

8. A priming method for use in a blood purification control apparatus used for a blood purification circuit that includes a hemofilter purifying blood, a blood removal line connected to a blood inlet of the hemofilter, and a blood return line connected to a blood outlet of the hemofilter,
the blood purification control apparatus comprising: a blood return valve for opening and closing the blood return line;
a first pump provided on a first line to pump a priming fluid to a part between the hemofilter and the blood return valve on the blood return line;
a first control unit configured to cause the priming fluid to enter the hemofilter from the blood outlet of the hemofilter, by closing the blood return valve and activating the first pump;
a second pump for (i) pumping the priming fluid to the hemofilter via the blood removal line and (ii) pumping the priming fluid out of the hemofilter via the blood removal line, wherein the first control unit is configured to activate the first pump and the second pump together so that the priming fluid is pumped of the hemofilter;
a third pump provided on a second line to pump the priming fluid to the hemofilter via a dialysate inlet of the hemofilter; and
a third line connected to the first line and the second line to supply the priming fluid to the first pump and the third pump,
said priming method comprising:
a first step of closing the blood return valve on the blood return line; and
a second step of sending a priming fluid to the blood return line between the blood return valve and the hemofilter.

9. The priming method according to claim 8,
said priming method further comprising
a third step of sending the priming fluid taken out of the hemofilter to the blood removal line.

10. The priming method according to claim 9,
wherein an amount of the priming fluid sent to in said second step is greater than an amount of the priming fluid taken out in said third step.

11. The priming method according to claim 8, further comprising a fourth step of opening the blood return line, wherein said first step is executed after said second step and said fourth step.

12. The priming method according to claim 8,
wherein the blood purification circuit further includes a circulation line that has a chamber and that connects the blood return line to a blood removal line connected to a blood inlet of the hemofilter so that the hemofilter, the blood removal line, and the blood return line forms a circularly-arranged line, and
said priming method further comprising
a fifth step of opening the blood return valve after completing priming for the blood purification circuit to run the priming fluid, so that the priming fluid is circulated in the circularly-arranged line.

13. The priming method according to claim 8, further comprising a sixth step of sending the priming fluid to the hemofilter via a dialysate inlet of the hemofilter.

14. The priming method according to claim 13, further comprising a seventh step of taking the priming fluid out of the hemofilter via a dialysate outlet of the hemofilter after the priming fluid is filled in a part of the hemofilter in said sixth step, the part serving as a part of a dialysis circuit.

15. The priming method according to claim 14,
wherein the blood purification circuit further includes: a container to which the priming fluid taken out of the hemofilter via the dialysate outlet is sent; a dialysate discharge line connecting the dialysate outlet of the hemofilter to the container; and a discharge line in which the priming fluid accumulated in the container flows to be discharged, and
said priming method further comprising:
an eighth step of sending the priming fluid taken out of the hemofilter via the dialysate outlet to the container; and
a ninth step of discharging a part of the priming fluid sent to the container via the discharge line after said eighth step, so that an amount of priming fluid remaining in the container after is adjusted.

* * * * *